United States Patent
Song et al.

(10) Patent No.: US 9,388,276 B2
(45) Date of Patent: Jul. 12, 2016

(54) MONOMERS AND POLYMERS FOR FUNCTIONAL POLYCARBONATES AND POLY(ESTER-CARBONATES) AND PEG-CO-POLYCARBONATE HYDROGELS

(75) Inventors: Jie Song, Shrewsbury, MA (US); Jianwen Xu, Worcester, MA (US)

(73) Assignee: University of Massachusetts, Boston, MA (US)

( * ) Notice: Subject to any disclaimer, the term of this patent is extended or adjusted under 35 U.S.C. 154(b) by 218 days.

(21) Appl. No.: 14/000,869

(22) PCT Filed: Feb. 24, 2012

(86) PCT No.: PCT/US2012/026427
§ 371 (c)(1),
(2), (4) Date: Nov. 14, 2013

(87) PCT Pub. No.: WO2012/116250
PCT Pub. Date: Aug. 30, 2012

(65) Prior Publication Data
US 2014/0058058 A1  Feb. 27, 2014

Related U.S. Application Data

(60) Provisional application No. 61/446,997, filed on Feb. 25, 2011, provisional application No. 61/484,138, filed on May 9, 2011.

(51) Int. Cl.
| | | |
|---|---|---|
| C07D 319/06 | (2006.01) | |
| C07D 405/06 | (2006.01) | |
| C07D 405/14 | (2006.01) | |
| A61L 27/18 | (2006.01) | |
| C08G 64/18 | (2006.01) | |
| C07C 247/10 | (2006.01) | |
| C08G 64/02 | (2006.01) | |

(52) U.S. Cl.
CPC ............ C08G 64/0208 (2013.01); A61L 27/18 (2013.01); C07C 247/10 (2013.01); C07D 319/06 (2013.01); C07D 405/06 (2013.01); C07D 405/14 (2013.01); C08G 64/0241 (2013.01); C08G 64/0291 (2013.01); C08G 64/18 (2013.01); C08G 64/183 (2013.01)

(58) Field of Classification Search
CPC .. C07D 319/06; C07D 405/06; C07D 405/14; A61L 27/18; C08G 64/18; C07C 247/10
See application file for complete search history.

(56) References Cited

U.S. PATENT DOCUMENTS 4,916,193 A 4/1990 Tang et al.
6,093,792 A 7/2000 Gross et al.

FOREIGN PATENT DOCUMENTS

EP 2090592 A1 8/2009
WO 2007/003054 A1 1/2007

OTHER PUBLICATIONS

Wiseman et al., caplus an 2005:535298 (2005).*
GB 804988, caplus abstract AN 1959:121868.*
Yan et al., 2011, Journal of Controlled Release, 152, e249-250.*
Xu et al. 2, 2011, Chemistry—An Asian Journal, 6, 2730-2737.*
Xu et al., 2011, Macromolecules, 44, 2660-2667.*
Zhang et al., 2011, Macromolecules, 44, 1755-1759.*
PCT/US2012/026427, Int'l Search Report and Written Opinion (Jun. 21, 2012).
EP12749377, Supplementary European Search Report (Dec. 17, 2014).
Shi, et al., "Hemoglobin conjugated micelles based on triblock biodegradable polymer as artificial oxygen carriers", Biomaterials; vol. 30, No. 28, pp. 5077-5085 (Oct. 1, 2009).
George, et al., "An efficient organocatalytic route to the atorvastatin side-chain", Tetrahedron Letters; vol. 48, No. 48; pp. 8544-8546 (Oct. 31, 2007).
Wiseman, et al., "1-Deoxy-5-hydroxysphingolipids as new anticancer principles: An efficient procedrue for stereoselective syntheses of 2-amino-3,5-diols", Organic Letters, vol. 7, No. 15, pp. 3155-3157 (Jul. 1, 2005).
Hisao, et al., "Bromoallenes as allyl dication equivalents in the presence or absence of Palladium: Direct construction of bicyclic sulfamides containing five- to eight-membered rings by tandem cyclization of bromoallenes", Chemistry—A European Journal, vol. 13, No. 6, pp. 1692-1708 (Feb. 12, 2007).
Kazuyuki, et al, "Total synthesis of Leustroducsin B", The Journal of Organic Chemistry, vol. 73, No. 14, pp. 5360-5370 (Jul. 1, 2008).
Xu, et al., "Cytocompatible poly(ethylene glycol)-co-polycarbonate hydrogels cross-linked by Copper-free, strain-promoted click chemistry", Chemistry—An Asian Journal, vol. 6, No. 10, pp. 2730-2737 (Oct. 4, 2011).
Xu, et al., "A versatile monomer for preparing well-defined functional polycarbonates and poly(ester-carbonates)", Macromolecues, vol. 44, No. 8, pp. 2660-2667 (Apr. 26, 2011).
Daniels, et al., "Palladium-catalyzed asymmetric synthesis of 2-alkynyl oxacycles", Angewandete Chemie Int'l Ed., vol. 50, No. 48, pp. 11506-11510 (Nov. 25, 2011).
Anders, et al. "Synthesis of a difunctional orthogonal coupler for the preparation of carbohydrate-functionalized sP(EO-stat.PO) hydrogels", Macromolecular Bioscience, vol. 11, No. 9, pp. 1201-1210 (Jun. 16, 2011).
Anders, et al. "Synthesis and characterization of functional six-membered ring carbonates for the preparation of orthogonal couplers", E-Polymers, vol. 11, No. 1, pp. 1-19 (Dec. 2011).

* cited by examiner

*Primary Examiner* — Sun Jae Yoo
(74) *Attorney, Agent, or Firm* — Milstein Zhang & Wu LLC

(57) ABSTRACT

The invention generally relates to functional polymers and hydrogels. More particularly, the invention provides versatile monomers and polymers with well-defined functionalities, e.g., polycarbonates and poly(ester-carbonates), compositions thereof, and methods for making and using the same. The invention also provides cytocompatible poly(ethylene glycol)-co-polycarobonate hydrogels (e.g., crosslinked by copper-free, strain-promoted "click" chemistry).

2 Claims, 20 Drawing Sheets

MONOMERS AND POLYMERS FOR FUNCTIONAL POLYCARBONATES AND POLY(ESTER-CARBONATES) AND PEG-CO-POLYCARBONATE HYDROGELS

PRIORITY CLAIMS AND RELATED PATENT APPLICATIONS

This application is the national phase of PCT/US12/26427, filed on Feb. 24, 2012, which claims the benefit of priority from U.S. Provisional Application Ser. No. 61/446,997, filed on Feb. 25, 2011, and U.S. Provisional Application Ser. No. 61/484,138, filed on May 9, 2011, the entire content of which is incorporated herein by reference in its entirety.

GOVERNMENT RIGHTS

The United States Government has certain rights to the invention pursuant to Grant No. R01AR055615 and R01GM088678 from National Institute of Health to the University of Massachusetts Medical School.

TECHNICAL FIELD OF THE INVENTION

The invention generally relates to functional polymers and hydrogels. More particularly, the invention relates to versatile monomers and polymers with well-defined functionalities, e.g., polycarbonates and poly(ester-carbonates), compositions thereof, and methods for making and using the same. The invention also relates to cytocompatible poly(ethylene glycol)-co-polycarobonate hydrogels (e.g., crosslinked by copper-free, strain-promoted "click" chemistry).

BACKGROUND OF THE INVENTION

Biodegradable polymers are useful in a variety of applications, for example, in controlled drug delivery, tissue engineering and medical devices. Advanced biomedical applications require biomaterials to not only provide necessary structural/mechanical support and biodegradability over an appropriate time frame, but also to possess defined chemical and biochemical properties to positively interact with the living system. Biocompatible and biodegradable polymers that share core structural features while exhibiting incremental variations in chemical functionalities and physical properties are valuable for screening optimal drug delivery vehicles and tissue engineering scaffolds. (Hook, et al. *Biomaterials* 2010, 31, 187; Hubbell, *Nat. Biotechnol.* 2004, 22, 828.)

Macromolecular architectures and compositions with a range of mechanical properties and degradation profiles have been reported. (Nair, et al. *Prog. Polym. Sci.* 2007, 32, 762; Sodergard, et al. *Prog. Polym. Sci.* 2002, 27, 1123.) For example, aliphatic polycarbonates have attracted increasing interest due to their non-acidic degradation products and potential to introduce properties complementary to those obtainable by other degradable polymers. (Pego, et al. *J. Biomater. Sci., Polym. Ed.* 2001, 12, 35; Pego, et al. *Macromol. Biosci.* 2002, 2, 411; Rokicki, *Prog. Polym. Sci.* 2000, 25, 259; Bat, et al. *Biomaterials* 2010, 31, 8696; Dankers, et al. *Macromolecules* 2006, 39, 8763; Zhu, et al. *Macromolecules* 1991, 24, 1736.) The hydrophobic nature and the lack of side chain functionalities of polycarbonates, however, have limited their biomedical applications. (Zelikin, et al. *Biomacromolecules* 2006, 7, 3239.) Indeed, such limitations are shared by synthetic biodegradable polymers in general, including polyesters, polyanhydrides, and polyorthoesters. (Vert, *Biomacromolecules* 2005, 6, 538; Rasal, et al. *Prog. Polym. Sci.* 2010, 35, 338; Kumar, et al. *Adv. Drug Delivery Rev.* 2002, 54, 889.)

Current methods for imparting functionalities and improving the hydrophilicity of biodegradable polymers include post-polymerization surface irradiation grafting, post-polymerization end-group modification, polymerization initiated by hydrophilic/functional polymer precursors, and (co)polymerization of functional monomers. (Edlund, et al. *J. Am. Chem. Soc.* 2005, 127, 8865; Suriano, et al. *J. Polym. Sci., Part A: Polym. Chem.* 2010, 48, 3271; He, et al. *Biomacromolecules* 2006, 7, 252; Zhang, et al. *J. Controlled Release* 2006, 112, 57; Gautier, et al. *J. Biomater. Sci.*, Polym. Ed. 2003, 14, 63; Lu, et al. *Macromolecules* 2010, 43, 4943; Trollsas, et al. *Macromolecules* 2000, 33, 4619; Jiang, et al. *Abstr. Papers Am. Chem. Soc.* 2005, 230, U4073; Gerhardt, et al. *Biomacromolecules* 2006, 7, 1735; Hu, et al. *Biomacromolecules* 2008, 9, 553; Pratt, et al. *Chem. Commun.* 2008, 114; Hu, et al. *J. Polym. Sci., Part A: Polym. Chem.* 2008, 46, 7022; Hu, et al. *J. Polym. Sci., Part A: Polym. Chem.* 2007, 45, 5518; Xie, et al. *J. Polym. Sci., Part A: Polym. Chem.* 2007, 45, 1737; Lou, et al. *Macromol. Rapid Commun.* 2003, 24, 161; Detrembleur, et al. *Macromolecules* 2000, 33, 14; Rieger, et al. *Macromolecules* 2004, 37, 9738; Yin, et al. *Macromolecules* 1999, 32, 7711.)

(Co)Polymerization of functional monomers provides a straightforward way to introduce functionalities and hydrophilicity with better-controlled polymer compositions and structures provided that suitable monomers could be designed. (Trollsas, et al. *Macromolecules* 2000, 33, 4619; Gerhardt, et al. *Biomacromolecules* 2006, 7, 1735.) However, due to the incompatibility of most reactive groups (e.g. hydroxyls, amines, carboxyls, and thiols) with the polymerization conditions, cumbersome protection and post-polymerization deprotection steps involving heavy metal catalysts and lowering overall yields are often required. (Trollsas, et al. *Macromolecules* 2000, 33, 4619; Hu, et al. *Biomacromolecules* 2008, 9, 553; Vandenberg, et al. *Macromolecules* 1999, 32, 3613; Zhang, et al. *Macromolecules* 2009, 42, 1010; Noga, et al. *Biomacromolecules* 2008, 9, 2056; Hu, et al. *J. Polym. Sci., Part A: Polym. Chem.* 2008, 46, 7022; Sanda, et al. *Macromolecules* 2001, 34, 1564; Kimura, et al. *Macromolecules* 1988, 21, 3338; Al-Azemi, et al. *Macromolecules* 1999, 32, 6536; Pounder, et al. *Biomacromolecules* 2010, 11, 1930.) The degradable nature of the backbone of these polymers also imposes additional challenges to the preparation of well-defined functional derivatives.

Although several monomers with "clickable" functionalities including alkyne- and (methyl)acrylate-containing lactones or carbonates have been reported, a pressing need exists for monomers functionalized with reactive groups orthogonal to polymerization conditions that enable facile post-polymerization functionalization without tedious protection/deprotection. (Parrish, et al. *J. Am. Chem. Soc.* 2005, 127, 7404; Han, et al. *Macromol. Biosci.* 2008, 8, 638; Jiang, et al. *Macromolecules* 2008, 41, 1937; Darcos, et al. *Polymer Chemistry* 2010, 1, 280; van der Ende, et al. *Macromolecules* 2010, 43, 5665; Chen, et al. *Macromolecules* 2010, 43, 201; Iha, et al. *Chem. Rev.* 2009, 109, 5620; Sumerlin, et al. *Macromolecules* 2010, 43, 1.)

Biocompatible hydrogels are important materials in biomedical research and pharmaceutical products. (Jen, et al. *Biotechnol. Bioeng.* 1996, 50, 357; Wang, et al. *Adv. Drug Delivery Rev.* 2010, 62, 699; Gkioni, et al. *Tissue Eng. Part B-Rev* 2010, 16, 577; Hynd, et al. *Biomater. Sci., Polym. Ed.* 2007, 18, 1223; Ifkovits, et al. *Tissue Eng.* 2007, 13, 2369; Khetan, et al. *Soft Matter* 2011, 7, 830; Kim, et al. *Tissue*

Engineering and Regenerative Medicine 2011, 8, 117; Lee, et al. *Chem. Rev.* 2001, 101, 1869.) Biocompatible hydrogels have been used as protein microchips, drug and gene delivery carriers, ophthalmic prostheses, and scaffolds for encapsulating cells to facilitate either the investigation of cell-extracellular matrix interactions or tissue regenerations. (Bertone, et al. *FEBS J.* 2005, 272, 5400; Hoare, et al. *Polymer* 2008, 49, 1993; Alvarez-Lorenzo, et al. *J. Drug Deliv. Sci. Tec.* 2010, 20, 237; Drury, et al. *Biomaterials* 2003, 24, 4337; Tessmar, et al. *Adv. Drug Delivery Rev.* 2007, 59, 274; Burdick, et al. *Adv. Mater.* 2011, 23, H41; Minh, et al. *Macromolecular Bioscience* 2010, 10, 563; Marklein, et al. *Adv. Mater.* 2010, 22, 175; Anderson, et al. *Biomaterials* 2011, 32, 3564; Benoit, et al. *Nat. Mater.* 2008, 7, 816; Haines-Butterick, et al. *Proc. Natl. Acad. Sci. U.S.A.* 2007, 104, 7791; Chung, et al. *Tissue Engineering Part A* 2009, 15, 243; Annabi, et al. *Tissue Eng. Part B-Rev* 2010, 16, 371.) Naturally occurring biopolymers such as collagens, fibrin, alginate, agarose, hyaluronan and chondroitin sulfate, as well as synthetic polymers such as polyethylene glycol) (PEG), polyvinyl alcohol) (PVA), poly (N-isopropylacrylamine) (PNIPAAM) have been used for regenerative medicine applications. (Drury, et al. *Biomaterials* 2003, 24, 4337.)

The chemistry, microstructure and physical properties of hydrogel tissue scaffolds have significant influences on the fate of their resident cells. (Lutolf, et al. *Nature* 2009, 462, 433; Even-Ram, et al. *Cell* 2006, 126, 645; Cushing, et al. *Science* 2007, 316, 1133.) Synthetic hydrogels present unique advantages over naturally occurring hydrogels due to the broader tunability of the properties of the former. (Kloxin, et al. *Science* 2009, 324, 59; Lee, et al. *Biomaterials* 2006, 27, 5268; Luo, et al. *Nature Materials* 2004, 3, 249.) Challenges still exist, however, for the translation of existing synthetic hydrogels for biomedical uses. For instance, the gelling of most physically crosslinked hydrogels requires substantial changes in environmental conditions (e.g., pH, temperature, ionic strength), which can be detrimental to the in situ encapsulated cells. In addition, the integrity of these physically crosslinked cell-gel constructs are difficult to maintain in vivo. On the other hand, the cytotoxicity of crosslinking reagents and initiators used for chemically crosslinked hydrogels can negatively impact the viability and long-term fate of the encapsulated cells. (Mann, et al. *Biomaterials* 2001, 22, 3045; Rouillard, et al. *Tissue Engineering Part C-Methods* 2011, 17, 173; Shu, et al. *Biomaterials* 2003, 24, 3825.)

In general, chemical crosslinking conditions and chemically crosslinked networks deemed cyto-compatible are still limited. (Hennink, et al. *Adv. Drug Delivery Rev.* 2002, 54, 13.) Among them, PEG-based hydrogels formed by photo-initiated radical polymerization of (meth)acrylated PEG macromers have been the most utilized for the encapsulation and support of tissue-specific differentiation of stem cells. Major limitations associated with photo-crosslinked PEG gels include the intrinsic heterogeneities of the network structures due to the uncontrolled radical polymerization process and the varied degrees of cytotoxicity of the aqueous radical initiators utilized (e.g., 1-2959 and VA-086). (Rouillard, et al. *Tissue Engineering Part C-Methods* 2011, 17, 173.) Alternative in situ crosslinking strategies involving disulfide bond formations or Michael addition reactions between thiols and acryaltes or vinyl sulfones can eliminate the need for radical initiators, but still suffer from the potential interference from the thiol residues widely present within the tissue environment.

Thus, a hydrogel system that can be crosslinked under physiological conditions without external perturbations or cross-reactivities with cellular or tissue environment is highly desired. For tissue regeneration applications, the hydrogels should also ideally possess adequate mechanical properties and exhibit tunable degradation rates potentially matching with those of the tissue integrations.

SUMMARY OF THE INVENTION

The invention is based, in part, on certain novel carbonate-based monomers, their controlled homopolymerization and copolymerization, and the facile functionalization of the resulting polycarbonates and poly(ester-carbonates), for example, via copper-catalyzed (CuAAC) and strain-promoted (SPAAC) azido-alkyne cycloaddition "click" chemistries. (Kolb, et al. *Angew. Chem.*, Int. Ed. 2001, 40, 2004; Agard et al. *J. Am. Chem. Soc.* 2004, 126, 15046.)

In one aspect, the invention generally relates to a compound having the structural formula of:

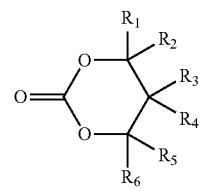

wherein, each of $R_1$, $R_2$, $R_3$, $R_4$, $R_5$ and $R_6$ independently is hydrogen, an alkyl, an alkoxy, —OH, a halide, an aryl, an aryloxy, an acyl, a haloalkyl group, provided that one or more of $R_1$, $R_2$, $R_3$, $R_4$, $R_5$ and $R_6$ independently is $R_x$, wherein $R_x$ is a group that comprises either an azide group or an alkynyl group.

In certain preferred embodiments, $R_x$ is:

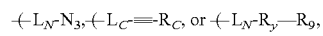

wherein $L_N$ is a linking group, $L_C$ is a linking group, $R_C$ is a hydrogen or a linear or branched, unsubstituted or substituted alkyl group, $R_y$ is a coupling moiety, and $R_9$ is a pendant group, and one or more of the carbon atom may be optionally substituted with a hetero-atom selected from O, S and N or with a —(C═O)— group.

In certain preferred embodiments, two of $R_1$, $R_2$, $R_3$, $R_4$, $R_5$ and $R_6$ are independently $R_x$ and the rest are hydrogen, for example, wherein $R_3$ and $R_4$ are $R_x$:

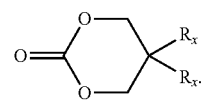

In certain preferred embodiments, one of $R_1$, $R_2$, $R_3$, $R_4$, $R_5$ and $R_6$ is $R_x$ and the rest are hydrogen, for example, where $R_3$ is $R_x$:

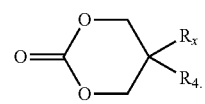

In another aspect, the invention generally relates to a monomer unit having the structure of:

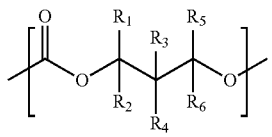

wherein each of $R_1$, $R_2$, $R_3$, $R_4$, $R_5$ and $R_6$ independently in hydrogen, an alkyl, an alkoxy, —OH, a halide, an aryl, an aryloxy, an acyl, a haloalkyl, provided that one or more of $R_1$, $R_2$, $R_3$, $R_4$, $R_5$ and $R_6$ independently is independently $R_x$, wherein $R_x$ is a group that comprises either an azide group or an alkynyl group.

In certain preferred embodiments, two of $R_1$, $R_2$, $R_3$, $R_4$, $R_5$ and $R_6$ independently is $R_x$, for example,

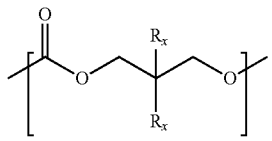

In certain preferred embodiments, one of $R_1$, $R_2$, $R_3$, $R_4$, $R_5$ and $R_6$ is $R_x$, for example,

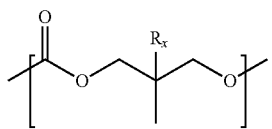

In yet another aspect, the invention generally relates to a polymer comprising a structural unit of:

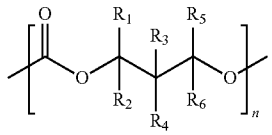

wherein each of $R_1$, $R_2$, $R_3$, $R_4$, $R_5$, and $R_6$ independently in hydrogen, an alkyl, an alkoxy, —OH, a halide, an aryl, an aryloxy, an acyl, a haloalkyl group, provided that one or more of $R_1$, $R_2$, $R_3$, $R_4$, $R_5$, and $R_6$ independently is independently $R_x$, wherein $R_x$ is a group that comprises either an azide group or an alkynyl group; and n is an integer from about 1 to about 2,000 (e.g., 1, 5, 10, 20, 50, 100, 200, 500, 1000, 2000).

In yet another aspect, the invention generally relates to a co-polymer comprising the monomer units of:

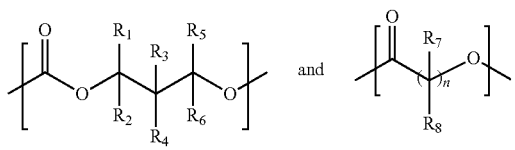

wherein each of $R_1$, $R_2$, $R_3$, $R_4$, $R_5$ and $R_6$ independently in hydrogen, an alkyl, an alkoxy, —OH, a halide, an aryl, an aryloxy, an acyl, a haloalkyl group, provided that one or more of $R_1$, $R_2$, $R_3$, $R_4$, $R_5$ and $R_6$ independently is independently $R_x$, wherein $R_x$ is a group that comprises either an azide group or an alkynyl group; each of $R_7$ and $R_8$ is independently hydrogen or an alkyl group; and n is an integer, for example, from about 1 to about 16 (e.g., 1, 2, 3, 4, 5, 6, 7, 8, 9, 10, 11, 12, 13, 14, 15, 16).

In yet another aspect, the invention generally relates to a method for preparing a hydrogel of poly(ethylene glycol)-co-polycarbonate. The method includes: (1) providing a first poly(ethylene glycol) macromer comprising a poly(ethylene glycol) oligomer segment and a flanking segment on one or more side thereof, wherein each flanking segment comprises a single- or multi-azido-functionalized biodegradable polycarbonate block; (2) providing a second poly(ethylene glycol) macromer comprising a poly(ethylene glycol) oligomer segment and a flanking segment on one or more side thereof, wherein each flanking segment comprises a terminal alkyne group; and (3) forming a hydrogel by crosslinking the first macromer and the second macromer under conditions so as to effect azide-alkyne cycloaddition.

In certain preferred embodiments, the method further includes: providing cells prior to the crosslinking step; and crosslinking the first macromer and the second macromer in the presence of cells under conditions so as to effect copper-free, strain-promoted azide-alkyne cycloaddition.

In certain preferred embodiments, the first poly(ethylene glycol) macromer has the structural formula of:

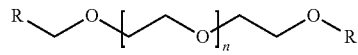

wherein each R is a group that comprises either an azide group or an alkynyl group, and n is an integer from about 0 to about 5,000 (e.g., 0, 1, 5, 10, 20, 50, 100, 500, 1,000, 2,000, 5,000). For example, each R may independently be

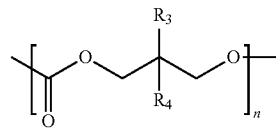

wherein each of $R_3$ and $R_4$ independently in hydrogen, an alkyl, an alkoxy, —OH, a halide, an aryl, an aryloxy, an acyl, a haloalkyl group, provided that one or both of $R_3$ and $R_4$ independently is independently $R_x$, wherein $R_x$ is a group that comprises either an azide group or an alkynyl group, and n is an integer from about 1 to about 2,000 (e.g., 1, 5, 10, 20, 50, 100, 200, 500, 1000, 2000).

In certain embodiments, the second poly(ethylene glycol) macromer has the general structural formula of:

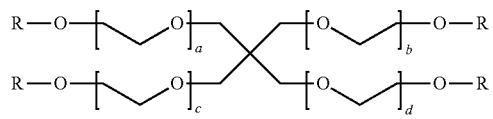

wherein R is

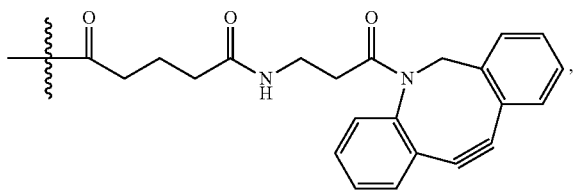 [SMILES: *C(=O)CCCC(=O)NCCC(=O)N1Cc2ccccc2C#Cc2ccccc21]

and each of a, b, c, and d is an integer and from about 1 to about 2000 (e.g., 1, 5, 10, 20, 50, 100, 200, 500, 1000, 2000).

In yet another aspect, the invention generally relates to a hydrogel composition that includes a hydrogel composition comprising a crosslinked product of a first macromer and a second macromere. The first macromer comprises a water-soluble hydrophilic polymer segment and a flanking segment on one or more side thereof, wherein each flanking segment comprises a single- or multi-azido-functionalized biodegradable polycarbonate block. The second macromer comprises a water-soluble hydrophilic polymer segment and a flanking segment on one or more side thereof, wherein each flanking segment comprises a terminal alkyne group.

In certain preferred embodiments, the first macromer is a first poly(ethylene glycol) macromer and the second macromer is a second poly(ethylene glycol) macromere. The first poly(ethylene glycol) macromer comprises a poly(ethylene glycol) oligomer segment and a flanking segment on one or more side thereof, wherein each flanking segment comprises a single- or multi-azido-functionalized biodegradable polycarbonate block. The second poly(ethylene glycol) macromer comprises a poly(ethylene glycol) oligomer segment and a flanking segment on one or more side thereof, wherein each flanking segment comprises a terminal alkyne group.

In yet another aspect, the invention generally relates to a cytocompatible hydrogel composition suitable for use in tissue repair or regeneration, comprising a three-dimensional construct of cells and a crosslinked network of a first poly (ethylene glycol) macromer and a second poly(ethylene glycol) macromere. The first poly(ethylene glycol) macromer comprises a poly(ethylene glycol) oligomer segment and a flanking segment on one or more side thereof, wherein each flanking segment comprises a single- or multi-azido-functionalized biodegradable polycarbonate block. The second poly(ethylene glycol) macromer comprises a poly(ethylene glycol) oligomer segment and a flanking segment on one or more side thereof, wherein each flanking segment comprises a terminal alkyne group.

The invention encompasses any product that is comprised of a polymer or co-polymer disclosed herein including any product prepared from a polymer or co-polymer of disclosed herein such as by post-polymerization functionalization. The invention also encompasses any product that is comprised of a hydrogel (with or without encapsulated cells) disclosed herein including any product prepared from a hydrogel disclosed herein such as by post-polymerization functionalization.

DEFINITIONS

Figure 1:
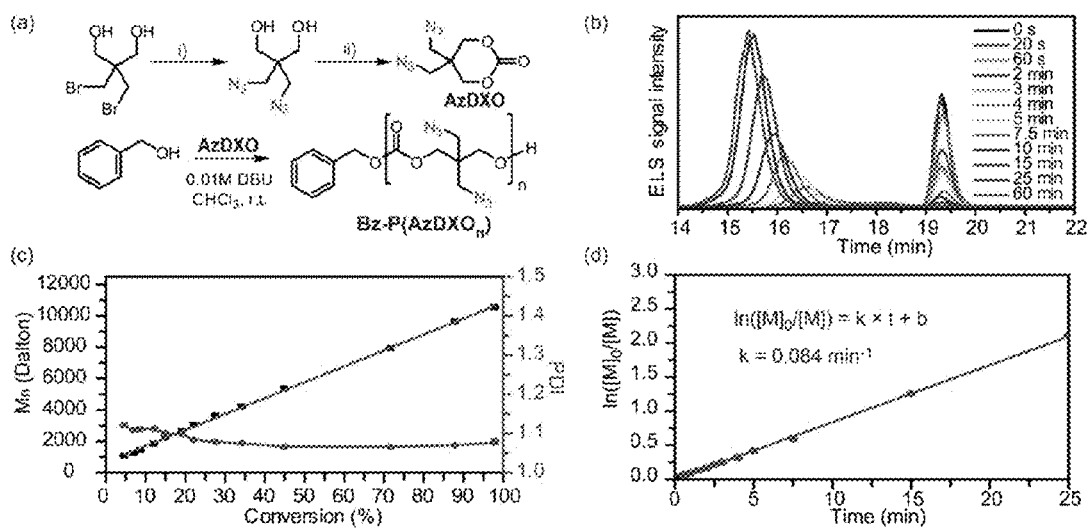
FIG. 1 shows the synthesis and polymerization kinetics of azido-functionalized cyclic carbonate monomer AzDXO.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, monomers and polymers, as described herein, may be substituted with any number of substituents or functional moieties.

The term ($C_x$-$C_y$), as used herein, refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_5$, $C_2$-$C_3$, $C_2$-$C_4$, $C_2$-$C_5$, $C_2$-$C_6$, and all like combinations. ($C_1$-$C_{20}$) and the likes similarly encompass the various combinations between 1 and 20 (inclusive) carbon atoms, such as ($C_1$-$C_6$), ($C_1$-$C_{12}$) and ($C_3$-$C_{12}$).

The term "acyl," as used herein, refers to alkanoyl group —C(=O)R$_d$, where R$_d$ is alkyl, alkenyl, alkynyl, aryl or aralkyl.

The term "alkoxy," as used herein, refers to the ether-O-alkyl, wherein alkyl is defined herein. The term "($C_x$-$C_y$)alkoxy" refers to a straight or branched chain alkyl group consisting essentially of from x to y carbon atoms that is attached to the main structure via an oxygen atom, wherein x is an integer from 1 to about 10 and y is an integer from about 2 to about 20. For example, "($C_1$-$C_{20}$)alkoxy" refers to a straight or branched chain alkyl group having 1-20 carbon atoms that is attached to the main structure via an oxygen atom, thus having the general formula alkyl-O—, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

The term "alkyl," as used herein, refers to saturated aliphatic groups including straight chain, branched chain, and cyclic groups all of them may be optionally substituted. As used herein, the term "($C_x$-$C_y$)alkyl" refers to a saturated linear or branched free radical consisting essentially of x to y carbon atoms, wherein x is an integer from 1 to about 10 and y is an integer from about 2 to about 20. Exemplary ($C_x$-$C_y$) alkyl groups include "($C_1$-$C_{20}$)alkyl," which refers to a saturated linear or branched free radical consisting essentially of 1 to 20 carbon atoms and a corresponding number of hydrogen atoms. Other examples include ($C_1$-$C_6$)alkyl, ($C_1$-$C_{12}$) alkyl ($C_1$-$C_{16}$)alkyl groups. Preferred alkyl groups contain 1 to 16 carbon atoms (e.g., "1-12 carbon atoms"). Suitable alkyl groups include methyl, ethyl and the like, and may be optionally substituted.

The term "alkynyl," as used herein, refers to unsaturated hydrocarbon groups which contain at least one carbon-carbon triple bond and includes straight chain and branched chain groups which may be optionally substituted. Preferred alkynyl groups have two to eighteen carbon atoms. Preferable alkynyl groups have two to twelve carbons. Suitable alkynyl groups include ethylnyl, propynyl and the like, and may be optionally substituted.

The term "amino," as used herein, refers to —NR$_a$R$_b$, where R$_a$ and R$_b$ are independently hydrogen, lower alkyl or an acyl group.

The term "aryl," as used herein, refers to aromatic groups which have at least one ring having a conjugated pi electron system and includes carbocyclic aryl, biaryl, both of which may be optionally substituted. As used herein, the term "(C$_x$-C$_y$)aryl" refers to an aromatic group consisting essentially of x to y carbon atoms in the aromatic ring(s), wherein x is an integer from about 6 to about 10 and y is an integer from about 10 to about 14. For example, "(C$_6$-C$_{10}$)aryl" refers to an aromatic group consisting essentially of 6 to 10 ring carbon atoms, e.g., phenyl and naphthyl. Preferred aryl groups have 6 to 10 carbon atoms. Suitable aryl groups include phenyl and napthyl.

The term "aryloxy," as used herein, refers to the ether-O-aryl, wherein aryl is defined herein.

The term "azide," as used herein, refers to the group —N$_3$ (or —N=N$^+$=N$^-$).

The term "haloalkyl," as used herein, refers to an alkyl substituted with one or more halogens.

The term "hydrocarbyl", as used herein, refers to a group primarily composed of hydrogen and carbon atoms and is bonded to the remainder of the molecule via a carbon atom, but it does not exclude the presence of other atoms or groups in a proportion insufficient to detract from the substantial hydrocarbon characteristics of the group. The hydrocarbyl group may be composed of only hydrogen and carbon atoms, for example, an aliphatic group such as alkyl or alkylene group groups, which may be linear or branched.

The term "optionally substituted" or "substituted," as used herein and unless otherwise specifically defined herein, refers to groups substituted by one to five substituents, independently selected from lower alkyl (acyclic and cyclic), aryl, alkenyl, akynyl, alkoxy, halo, haloalkyl, amino, aminoalkyl, mercapto, alkylthio, nitro, alkanoyl, alkanoyloxy, alkanoyloxyalkanoyl, alkoxycarboxy, carbalkoxy, carboxamido, formyl, carboxy, hydroxy, cyano, azido, keto and cyclic ketals thereof, alkanoylamido and hemisuccinate ester salts.

DETAILED DESCRIPTION OF THE INVENTION

The invention is based, in part, on the unexpected discovery and syntheses of novel carbonate-based monomers (e.g., azido-substituted cyclic trimethylene carbonate-based monomers) their controlled homopolymerization and copolymerization (e.g., with lactide), and the facile functionalization of the resulting polycarbonates and poly(ester-carbonates), for example, via copper-catalyzed (CuAAC) and strain-promoted (SPAAC) azido-alkyne cycloaddition "click" chemistries. The invention is also based, in part, on the unexpected discovery of novel and efficient methods for preparing cytocompatible poly(ethylene glycol)-co-polycarbonate hydrogels, for example, crosslinked by copper-free, strain-promoted "click" chemistry.

Monomers and Polymers for Well-Defined Functional Polycarbonates and Poly(Ester-Carbonates)

The invention enables the design, syntheses and application of versatile functional monomers that may be utilized for the preparation of functional polycarbonates and functional block and random poly(ester carbonate) copolymers. These polymers meet the requirements of (1) that the preparation of functional monomers in large scale with high purity without the need for chromatographic purifications, (2) that the reactive handles (in either protected or unmasked forms) of the monomers are compatible with the downstream polymerization conditions while the deprotection after polymerization can be carried out quantitatively under mild conditions if needed, and (3) that the accessibility and reactivity of the reactive handles of the monomers for post-polymerization modifications are high, ensuring efficient and quantitative functionalization. For example, the azido-substituted cyclic trimethylene carbonate monomers are readily polymerized to provide biodegradable polymers with pendent azido groups, which may be used as handles to introduce a wide range of functional groups via Huisgen 1,3-dipolar cycloaddition "click" chemistry. Other examples of high efficiency and fidelity "click" chemistry include Diels-Alder reaction, Michael addition, and thiol-ene reaction. Polymers (including copolymers) of the invention are useful in a variety of applications, for example, in tissue engineering, drug delivery, dental devices, sutures, vascular stents and other medical devices.

In one aspect, the invention generally relates to a compound having the structural formula of:

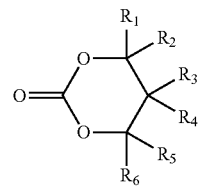

wherein, each of R$_1$, R$_2$, R$_3$, R$_4$, R$_5$ and R$_6$ independently is hydrogen, an alkyl, an alkoxy, —OH, a halide, an aryl, an aryloxy, an acyl, a haloalkyl group, provided that one or more of R$_1$, R$_2$, R$_3$, R$_4$, R$_5$ and R$_6$ independently is R$_x$, wherein R$_x$ is a group that comprises either an azide group or an alkynyl group.

In certain preferred embodiments, R$_x$ is:

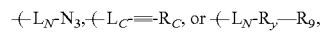

wherein L$_N$ is a linking group, L$_C$ is a linking group, R$_C$ is a hydrogen or a linear or branched, unsubstituted or substituted alkyl group, R$_y$ is a coupling moiety, and R$_9$ is a pendant group, and one or more of the carbon atom may be optionally substituted with a hetero-atom selected from O, S and N or with a —(C=O)— group.

In some embodiments, L$_N$ is a bivalent linear or branched, unsubstituted or substituted alkylene group, wherein one or more of the carbon atoms may be optionally substituted with a hetero-atom selected from O, S and N or with a —(C=O)— group.

In certain preferred embodiments, two of R$_1$, R$_2$, R$_3$, R$_4$, R$_5$ and R$_6$ are independently R$_x$ and the rest are hydrogen, for example, wherein R$_3$ and R$_4$ are R$_x$:

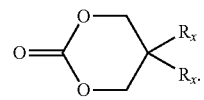

In certain preferred embodiments, one of R$_1$, R$_2$, R$_3$, R$_4$, R$_5$ and R$_6$ is R$_x$ and the rest are hydrogen, for example, where R$_3$ is R$_x$:

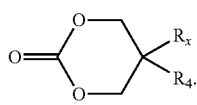

In certain preferred embodiments, each $R_x$ group independently is

Each $L_N$ may be independently a bivalent —(CH$_2$)$_p$— radical, wherein each p is independently an integer, for example, from about 1 to about 16 (e.g., 1, 2, 3, 4, 5, 6, 7, 8, 9, 10, 11, 12, 13, 14, 15, 16). Each $L_N$ may also be independently a bivalent —(O—CH$_2$)$_q$— radical, wherein each q is independently an integer, for example, from about 1 to about 16 (e.g., 1, 2, 3, 4, 5, 6, 7, 8, 9, 10, 11, 12, 13, 14, 15, 16).

In certain preferred embodiments, each $R_x$ independently is

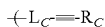

wherein $L_C$ and $R_C$ each may be a $C_1$-$C_{16}$ alkyl group.

In certain preferred embodiments, $R_x$ is:

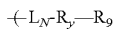

wherein each $L_N$ is independently a bivalent —(CH$_2$)$_p$— radical, wherein each p is independently an integer, for example, from about 1 to about 16. For example, $R_y$ may be

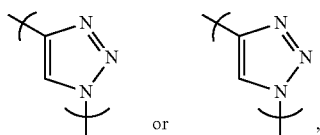

and $R_9$ can be

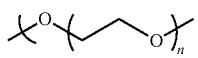

wherein n is an integer, for example, from about 0 to about 400 (e.g., 0, 1, 2, 3, 4, 5, 6, 7, 8, 9, 10, 20, 50, 100, 200, 300, 400).

$R_y$ may also be

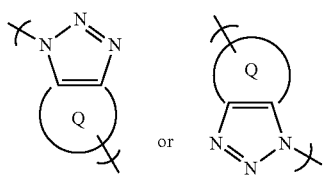

wherein Q is a substituted or unsubstituted cyclic group. Q may be a $C_3$-$C_{12}$ cyclic group, optionally with one or more of the carbon atoms may be optionally substituted with a heteroatom selected from O, S and N or with a —(C=O)— group.

For example, Q may have the structural formula of:

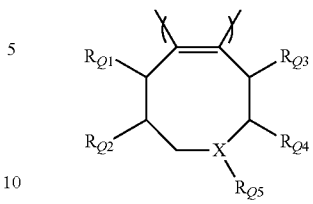

wherein each of $R_{Q1}$, $R_{Q2}$, $R_{Q3}$, $R_{Q4}$ and $R_{Q5}$ is independently a hydrogen, a halide, —OH, or a hydrocarbyl group and may optionally form one or more fused rings and X is carbon or a hetero-atom selected from O, S and N or a —(C=O)— group.

In some preferred embodiments, Q has the structural formula of:

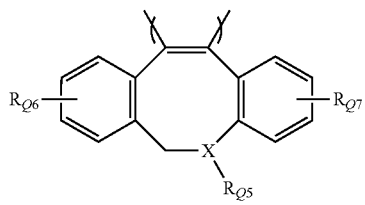

wherein each of $R_{Q5}$, $R_{Q6}$ and $R_{Q7}$ is independently a hydrogen, a halide, —OH, or a hydrocarbyl group.

In some preferred embodiments, Q has a structural formula selected from:

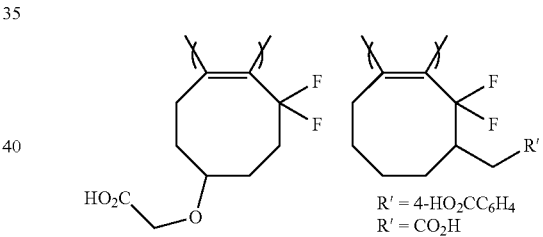

R' = 4-HO$_2$CC$_6$H$_4$
R' = CO$_2$H

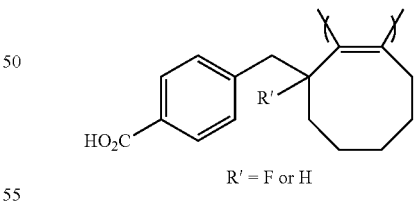

R' = F or H

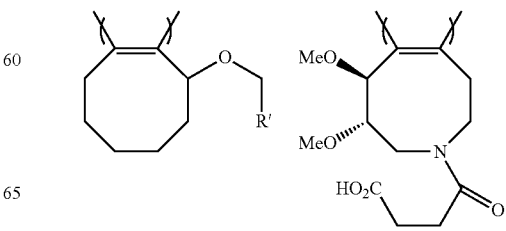

-continued

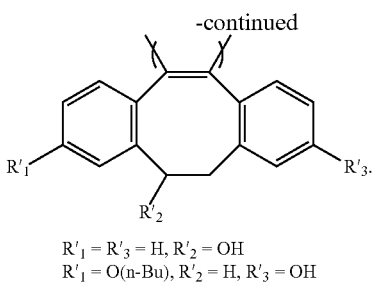

R'₁ = R'₃ = H, R'₂ = OH
R'₁ = O(n-Bu), R'₂ = H, R'₃ = OH

Other examples of Q include:

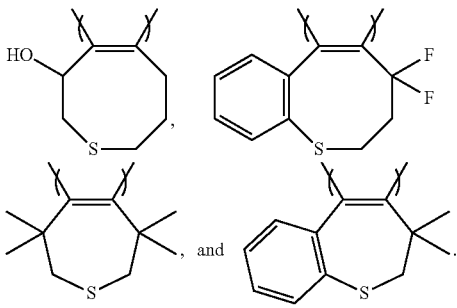

, and

In another aspect, the invention generally relates to a monomer unit having the structure of:

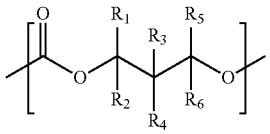

wherein each of $R_1$, $R_2$, $R_3$, $R_4$, $R_5$ and $R_6$ independently in hydrogen, an alkyl, an alkoxy, —OH, a halide, an aryl, an aryloxy, an acyl, a haloalkyl, provided that one or more of $R_1$, $R_2$, $R_3$, $R_4$, $R_5$ and $R_6$ independently is independently $R_x$, wherein $R_x$ is a group that comprises either an azide group or an alkynyl group.

In certain preferred embodiments, two of $R_1$, $R_2$, $R_3$, $R_4$, $R_5$ and $R_6$ independently is $R_x$, for example,

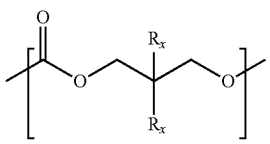

In certain preferred embodiments, one of $R_1$, $R_2$, $R_3$, $R_4$, $R_5$ and $R_6$ is $R_x$, for example,

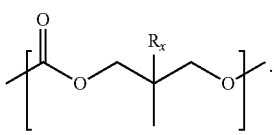

In yet another aspect, the invention generally relates to a polymer comprising a structural unit of:

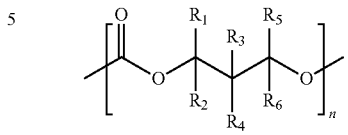

wherein each of $R_1$, $R_2$, $R_3$, $R_4$, $R_5$, and $R_6$ independently in hydrogen, an alkyl, an alkoxy, —OH, a halide, an aryl, an aryloxy, an acyl, a haloalkyl group, provided that one or more of $R_1$, $R_2$, $R_3$, $R_4$, $R_5$, and $R_6$ independently is independently $R_x$, wherein $R_x$ is a group that comprises either an azide group or an alkynyl group; and n is an integer from about 1 to about 2,000 (e.g., 1, 5, 10, 20, 50, 100, 200, 500, 1000, 2000).

In certain preferred embodiments, $R_x$ is:

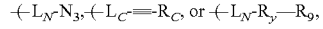

wherein $L_N$ is a linking group, $L_C$ is a linking group, $R_C$ is a hydrogen or a linear or branched, unsubstituted or substituted alkyl group, $R_y$ is a coupling moiety, and $R_9$ is a pendant group, and one or more of the carbon atom may be optionally substituted with a hetero-atom selected from O, S and N or with a —(C=O)— group.

In certain preferred embodiments, two of $R_1$, $R_2$, $R_3$, $R_4$, $R_5$ and $R_6$ independently is $R_x$, for example,

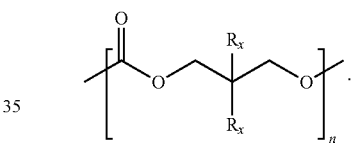

In certain preferred embodiments, one of $R_1$, $R_2$, $R_3$, $R_4$, $R_5$ and $R_6$ is $R_x$, for example,

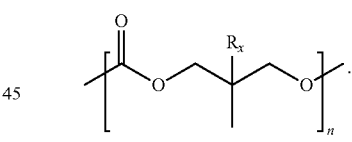

In yet another aspect, the invention generally relates to a co-polymer comprising the monomer units of:

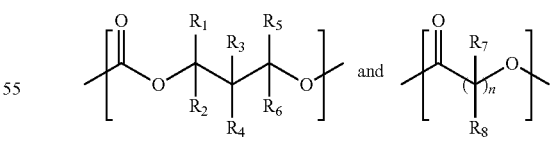

wherein each of $R_1$, $R_2$, $R_3$, $R_4$, $R_5$ and $R_6$ independently in hydrogen, an alkyl, an alkoxy, —OH, a halide, an aryl, an aryloxy, an acyl, a haloalkyl group, provided that one or more of $R_1$, $R_2$, $R_3$, $R_4$, $R_5$ and $R_6$ independently is independently $R_x$, wherein $R_x$ is a group that comprises either an azide group or an alkynyl group; each of $R_7$ and $R_8$ is independently hydrogen or an alkyl group; and n is an integer, for example, from about 1 to about 16 (e.g., 1, 2, 3, 4, 5, 6, 7, 8, 9, 10, 11, 12, 13, 14, 15, 16).

In certain preferred embodiments, $R_x$ is:

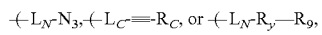

wherein $L_N$ is a linking group, $L_C$ is a linking group, $R_C$ is a hydrogen or a linear or branched, unsubstituted or substituted alkyl group, $R_y$ is a coupling moiety, and $R_9$ is a pendant group, and one or more of the carbon atom may be optionally substituted with a hetero-atom selected from O, S and N or with a —(C=O)— group.

The co-polymer may be a random co-polymer.

In certain embodiments, the co-polymer is a block co-polymer comprising blocks of:

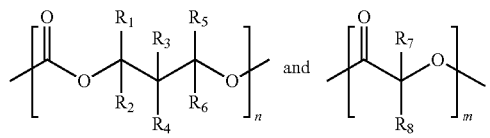

wherein m is an integer, for example, from about 1 to about 500 (e.g., 1, 3, 5, 10, 20, 50, 100, 200, 500). n is an integer, for example, from about 1 to about 500 (e.g., 1, 3, 5, 10, 20, 50, 100, 200, 500).

In certain embodiments, the molar ratio of

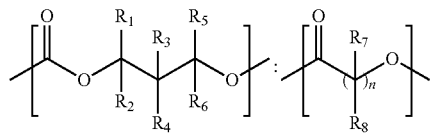

is from about 1:0.1 to about 0.1:1 (e.g., from about 0.05:1 to about 1:0.05, from about 0.1:1 to about 1:0.1, from about 0.5:1 to about 1:0.5, from about 0.8:1 to about 1:0.8).

The polymer and co-polymer of the invention may have a Mn from about 5,000 to about 100,000 (e.g., 5k, 10k, 20k, 50k, 100k).

The invention also encompasses any product that is comprised of a polymer or co-polymer disclosed herein including any product prepared from a polymer or co-polymer of disclosed herein such as by post-polymerization functionalization.

In yet another aspect, the invention generally relates to a three-dimensional scaffold comprising a polymer or co-polymer of the invention and optionally includes cells, for example, selected from osteoblasts, chondrocytes, endothelial cells, epithelial cells, embryonic stem cells, mesenchymal stem cells, hematopoietic stem cells, or cell lines.

The polymer and co-polymer of the invention may be polymerized using a small molecule initiator that includes an —OH, —SH or —NH$_2$ group, for example, $R_{sm}$—OH, $R_{sm}$—SH or $R_{sm}$—NH$_2$, wherein R is an unsubstituted or substituted alkyl group or aryl group and one or more carbon atoms of the alkyl or aryl group may be substituted with a hetero atom such as O, S or N. Non-limiting exemplary small molecule initiators include ethanol, benzyl alcohol, and ethylene glycol.

The polymer and co-polymer of the invention may be polymerized using a pre-polymer initiator that includes an —OH, —SH or —NH$_2$ group, for example, $R_{pp}$—OH, $R_{pp}$—SH or $R_{pp}$—NH$_2$, wherein $R_{pp}$ is an oligomeric or polymeric group.

The polymerization initiator, either a small molecule or a pre-polymer, may include two or a multiple of —OH, —SH or NH$_2$ groups. For example, a multi-functional initiator may generate polymerization products having branched, star- or web-shaped polymer products, In another aspect, the invention generally relates to a product that includes a polymer or a co-polymer of the invention.

The invention offers a number of distinct advantages. First, monomer preparation and purification are simple. Compared with existing functional monomers which usually involve multiple reaction steps with chromatographic purifications and low yields, the monomers of the invention can be prepared in good overall yield (e.g., about 50% or greater) with high purity (e.g., >99%) in just two steps, without the need for any chromatography.

Additionally, monomers of the invention are compatible with existing living polymerization techniques and may be polymerization in both melting and solution state catalyzed by metal catalysts or all-organic catalysts. The azido groups do not interfere with the polymerization step and are compatible with most existing ring-opening living polymerization catalytic systems. The monomers of the invention are also compatible with copolymerization with industrial monomers. For example, the monomers may be copolymerized with L-lactide, D,L-lactide, e-caprolactone, and glycolide, which are commonly used in industrial ROP processes.

Furthermore, homopolymers and copolymers of the invention are well-defined products, e.g., with high molecular weight (>10,000) and narrow polydispersity (PDI<1.1). Linear, branched and star architecture with random, block or multi-segment compositions may be prepared by choosing suitable initiator, co-monomer and monomer feeding ratios and sequences. For example, the azido-containing homopolymers and copolymers may be prepared that are stable up to 175° C., making them compatible with industrial thermal processing techniques.

Another distinctive advantage is that post-polymerization functionalization can be performed under mild conditions. For instance, the appended azido groups along the polymer backbone can be directly modified with small molecule, oligomers and biomacromolecules through copper-catalyzed or copper-free "click" chemistries with high fidelity under mild conditions. Degradation of polymers can be prevented under such mild conditions, especially those strain-promoted, copper-free "click" reactions that eliminate the use of toxic copper catalysts. Such an approach may be particularly attractive for making materials for in vivo applications.

Cytocompatible Poly(Ethylene Glycol)-Co-Polycarbonate Hydrogels

The invention also provides novel and efficient methods for preparing cytocompatible poly(ethylene glycol)-co-polycarbonate hydrogels, for example, crosslinked by copper-free, strain-promoted "click" chemistry. The invention discloses a facile method for preparing PEG macromers flanked with aliphatic azido-functionalized biodegradable polycarbonate blocks, which are subsequently crosslinked with dibenzylcocloctyne (DBCO)-terminated PEG macromers using copper-free, strain-promoted [3+2] azide-alkyne cylcloaddition (SPAAC). The choice of the SPAAC "click" chemistry as the in situ crosslinking strategy is to take advantage of the high fidelity and orthogonality of the reaction as well as its compatibility with physiological conditions. (Agard, et al. *J. Am. Chem. Soc.* 2005, 127, 11196; Baskin, et al. *Aldrichimica Acta* 2010, 43, 15.) Equally important, comparing to the copper-catalyzed [3+2] azide-alkyne cylcloaddition (CuAAC) that have been more broadly applied to the functionalization of hydrogels including PEG, PVA and hyaluronan, the copper-free SPAAC presents significant advantage in terms of both short-term cytocompatibility and long-term biocompatibility. (Malkoch, et al. *Chem. Commun.* 2006, 2774; Ossipov, et al. *Macromolecules* 2006, 39, 1709; Crescenzi, et al. *Biomacromolecules* 2007, 8, 1844.)

Although more biocompatible metal catalysts are being developed for CuAAC, their safety for in vivo tissue engineering applications remains unknown. By contrast, the SPAAC has already been utilized for live cell imaging, in vivo metabolic labelling in *C. elegans*, zebrafish and mice. (Amo, et al. *J. Am. Chem. Soc.* 2010, 132, 16893; Beatty, et al. *Chem Bio Chem* 2010, 11, 2092; Laughlin, et al. *ACS Chem. Biol.* 2009, 4, 1068; Laughlin, et al. *Science* 2008, 320, 664; Baskin, et al. *Proc. Natl. Acad. Sci. U.S.A.* 2010, 107, 10360; Chang, et al. *Proc. Natl. Acad. Sci. U.S.A.* 2010, 107, 1821.) Thus, it is not surprising that SPAAC has quickly caught the attention of the polymer/hydrogel and tissue engineering communities. (DeForest, et al. *Chem. Mater.* 2010, 22, 4783; DeForest, et al. *Nat. Mater.* 2009, 8, 659.)

The azido-functionalized polycarbonate blocks, which serve as SPAAC crosslinking sites, are grafted to the ends of the hydrophilic PEG using organocatalytic ring-opening polymerization (ROP) of an easy-to-prepare functional cyclic carbonate monomer, AzDXO, that was recently developed. (Xu, et al. *Macromolecules,* 44, 2660.) ROP of cyclic monomers has been used for preparing biodegradable polymers. Recent progress on the development of organocatalysts for ROP offers great potential for preparing hydrogels with reduced toxicity that are associated with traditional metal catalysts. (Kamber, et al. *Chem. Rev.* 2007, 107, 5813; Nederberg, et al. *Soft Matter* 2010, 6, 2006; Nederberg, et al. *Biomacromolecules* 2007, 8, 3294.) The previously demonstrated (co)polymerization versatility of AzDXO by living organocatalytic ROP under mild conditions (e.g., rt) and the facile functionalization of the side chains of the resulting polycarbonate P(AzDXO) via SPAAC under physiological conditions have opened the possibilities for adjusting the mechanical, biochemical and degradation properties of the PEG-co-P(AzDXO) hydrogels for regenerative medicine applications. (Xu, et al. *Macromolecules,* 44, 2660.)

Cytocompatible PEG-co-polycarobonate hydrogels crosslinked by water soluble PEG-P(AzDXO)$_{2m}$ macromers with varying PEG block lengths and linear or 4-armed DBCO-capped PEG macromers were prepared using copper-free SPAAC. The macromer components were non-cytotoxic, and the rapid gelling (as quick as <60 sec) enabled by the copper-free "click" chemistry allowed the encapsulation of bone-marrow derived stromal cells with higher cellular viability than the photo-crosslinked PEG6k-DMA gels commonly used for cartilage tissue engineering applications. The mechanical properties of these gels could be readily tuned by the adjusting macromer structures and the lengths of their constituent polymer blocks. The combination of cytocompatibility and tunable gelling rates and mechanical properties make these "clickable" gels appealing candidates as cell encapsulation strategies and as injectable formulations for minimally invasive tissue repair.

Thus, in yet another aspect, the invention generally relates to a method for preparing a hydrogel of poly(ethylene glycol)-co-polycarbonate. The method includes: (1) providing a first poly(ethylene glycol) macromer comprising a poly(ethylene glycol) oligomer segment and a flanking segment on one or more side thereof, wherein each flanking segment comprises a single- or multi-azido-functionalized biodegradable polycarbonate block; (2) providing a second poly(ethylene glycol) macromer comprising a poly(ethylene glycol) oligomer segment and a flanking segment on one or more side thereof, wherein each flanking segment comprises a terminal alkyne group; and (3) forming a hydrogel by crosslinking the first macromer and the second macromer under conditions so as to effect azide-alkyne cycloaddition.

In certain preferred embodiments, the method further includes: providing cells prior to the crosslinking step; and crosslinking the first macromer and the second macromer in the presence of cells under conditions so as to effect copper-free, strain-promoted azide-alkyne cycloaddition.

In some embodiments, the first poly(ethylene glycol) macromer and one or more of the flanking segments thereof independently includes a poly(carbonate) block. In some embodiments, the second poly(ethylene glycol) macromer and one or more of the flanking segments thereof independently comprises a poly(carbonate) block.

In certain preferred embodiments, the first poly(ethylene glycol) macromer has the structural formula of:

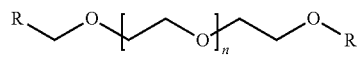

wherein each R is a group that comprises either an azide group or an alkynyl group, and n is an integer from about 0 to about 5,000 (e.g., 0, 1, 5, 10, 20, 50, 100, 500, 1,000, 2,000, 5,000). For example, each R may independently be

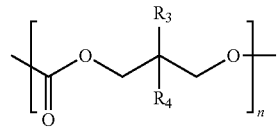

wherein each of $R_3$ and $R_4$ independently in hydrogen, an alkyl, an alkoxy, —OH, a halide, an aryl, an aryloxy, an acyl, a haloalkyl group, provided that one or both of $R_3$ and $R_4$ independently is independently $R_x$, wherein $R_x$ is a group that comprises either an azide group or an alkynyl group, and n is an integer from about 1 to about 2,000 (e.g., 1, 5, 10, 20, 50, 100, 200, 500, 1000, 2000).

In certain embodiments, the second poly(ethylene glycol) macromer has the general structural formula of:

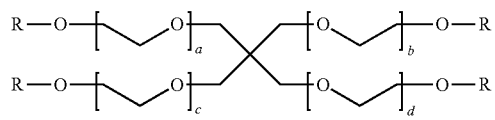

wherein R is

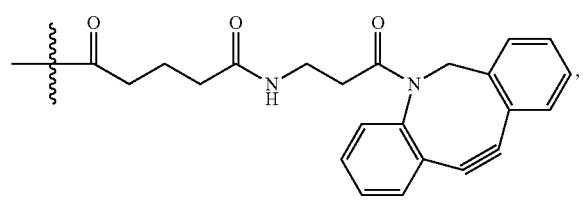 [SMILES: *C(=O)CCCC(=O)NCCC(=O)N1Cc2ccccc2C#Cc2ccccc21]

and each of a, b, c, and d is an integer and from about 1 to about 2000 (e.g., 1, 5, 10, 20, 50, 100, 200, 500, 1000, 2000).

In some embodiments, each of the flanking segment of the first poly(ethylene glycol) macromer comprises a multi-azido-functionalized biodegradable polycarbonate block. In some embodiments, each of the flanking segment of the second poly(ethylene glycol) macromer comprises an acyclic terminal alkyne group.

In some embodiments, each of the flanking segment of the second poly(ethylene glycol) macromer comprises a cyclic terminal alkyne group, for example, a dibenzylcyclooctyne (DBCO) group.

In certain preferred embodiments, crosslinking the first macromer and the second macromer is performed via copper-free, strain-promoted azide-alkyne cycloaddition. In some embodiments, crosslinking the first macromer and the second macromer is performed via copper-catalyzed azide-alkyne cycloaddition.

Any suitable biological cells may be encapsulated via methods disclosed herein, for example, mammalian cells including osteoblasts, chondrocytes, endothelial cells, epithelial cells, embryonic stem cells, mesenchymal stem cells, hematopoietic stem cells, or cell lines. In certain preferred embodiments, the encapsulated cells are bone marrow stromal cells or mesenchymal stem cells.

In yet another aspect, the invention generally relates to a hydrogel composition that includes a hydrogel composition comprising a crosslinked product of a first macromer and a second macromere. The first macromer comprises a water-soluble hydrophilic polymer segment and a flanking segment on one or more side thereof, wherein each flanking segment comprises a single- or multi-azido-functionalized biodegradable polycarbonate block. The second macromer comprises a water-soluble hydrophilic polymer segment and a flanking segment on one or more side thereof, wherein each flanking segment comprises a terminal alkyne group.

In certain preferred embodiments, the first macromer is a first poly(ethylene glycol) macromer and the second macromer is a second poly(ethylene glycol) macromere. The first poly(ethylene glycol) macromer comprises a poly(ethylene glycol) oligomer segment and a flanking segment on one or more side thereof, wherein each flanking segment comprises a single- or multi-azido-functionalized biodegradable polycarbonate block. The second poly(ethylene glycol) macromer comprises a poly(ethylene glycol) oligomer segment and a flanking segment on one or more side thereof, wherein each flanking segment comprises a terminal alkyne group.

In yet another aspect, the invention generally relates to a cytocompatible hydrogel composition suitable for use in tissue repair or regeneration, comprising a three-dimensional construct of cells and a crosslinked network of a first poly(ethylene glycol) macromer and a second poly(ethylene glycol) macromere. The first poly(ethylene glycol) macromer comprises a poly(ethylene glycol) oligomer segment and a flanking segment on one or more side thereof, wherein each flanking segment comprises a single- or multi-azido-functionalized biodegradable polycarbonate block. The second poly(ethylene glycol) macromer comprises a poly(ethylene glycol) oligomer segment and a flanking segment on one or more side thereof, wherein each flanking segment comprises a terminal alkyne group.

The invention also encompasses any product that is comprised of a hydrogel (with or without encapsulated cells) disclosed herein including any product prepared from a hydrogel disclosed herein such as by post-polymerization functionalization.

Examples

Monomers and Polymers for Well-Defined Functional Polycarbonates and Poly(Ester-Carbonates)

Monomer Design and Preparation.

High molecular weight polyesters and polycarbonates are usually prepared by ring-opening polymerization (ROP) of cyclic monomers. (Dechy-Cabaret, et al. *Chem. Rev.* 2004, 104, 6147.) Conventional catalysts and polymerization conditions employed in ROP could result in relatively broad molecular weight distributions and unexpected ether formations. (Rokicki, G. *Prog. Polym. Sci.* 2000, 25, 259; Ariga, et al. *Macromolecules* 1997, 30, 737.) Recent developments on organic catalysts for ROP have made it possible to prepare well-defined polyesters and polycarbonates (PDI<1.1) under mild conditions. (Nederberg, et al. *Biomacromolecules* 2007, 8, 153; Kamber, et al. *Chem. Rev.* 2007, 107, 5813.) A general method for preparing functional poly(ester-carbonates) with well-defined compositions and structures, however, is yet to be developed. Our goal is to develop an azido-functionalized cyclic carbonate monomer that exhibits ROP kinetics similar to that of the ROP of lactides under the same mild conditions enabled by organic catalyst 1,8-diazabicyclo[5.4.0]-undec-7-ene (DBU). Such an approximation of polymerization kinetics could enable poly(ester-carbonates) with both random and block architectures be prepared with well-defined compositions and narrow polydispersity. The choice of the azido functionality over alkyne or acrylate as a "clickable" group of the monomer is mainly inspired by its ability to withstand most basic and acidic conditions as well as temperatures up to 130° C. where alkynes and acrylates tended to self-crosslink or participate in free radical polymerizations. (Brase, et al. *Angew. Chem.*, Int. Ed. 2005, 44, 5188; Kuhling, et al. *Macromolecules* 1990, 23, 4192; Sumerlin, et al. *Macromolecules* 2005, 38, 7540.) In addition, the availability of many commercialized alkyne and cyclooctyne derivatives makes the post-polymerization functionalization with or without copper catalyst straightforward. Finally, the azido groups could also enable functionalizations via Staudinger ligation, which could be useful for certain biological investigations both in vitro and in vivo. (Baskin, et al. *Aldrichimica Acta* 2010, 43, 15; Saxon, et al. *Science* 2000, 287, 2007.)

For example, 5,5-bis(azidomethyl)-1,3-dioxan-2-one (AzDXO, FIG. 1a) was designed as the functional monomer. AzDXO was synthesized from 2,2-bis(bromomethyl)propane-1,3-diol in 2 steps with an overall yield of 45.6%. High purity (>99%) product was obtained by recrystallization purification. Despite its high azido content, the monomer was safe to handle during room temperature. No decomposition or explosion was observed when it was vacuum-dried at 90° C. for 2 days, although like all azido compounds, this monomer should always be handled with precaution.

FIG. 1 shows the synthesis and polymerization kinetics of azido-functionalized cyclic carbonate monomer AzDXO. (a) AzDXO was synthesized in 2 steps in 45.6% overall yield: i) $NaN_3$, DMSO, 110° C., 16 h; ii) ethyl chloroformate, THF, ice bath 4 h, rt (room temperature) 12 h. Ring opening polymerization of AzDXO was carried out in $CDCl_3$ at rt using benzyl alcohol (Bz) as an initiator and 1,8-Diazabicyclo[5.4.0]-undec-7-ene (DBU) as a catalyst. $[AzDXO]_0=1.0$ M; $[AzDXO]_0$: [Bz]: [DBU]=50:1:0.01. (b) GPC monitoring of polymerization by evaporative light scattering (ELS) detector over time; (c) Polymerization kinetics determined from GPC showing linear increase of number-average molecular weight ($M_n$) and consistent low polydispersity (PDI) with the increase of monomer conversion, respectively. (d) Plot of ln([M]$_0$/[M]) vs time (t) showing a linear first-order kinetics for the ROP of AzDXO, supporting a controlled/"living" polymerization mechanism. [M]$_0$ and [M] are the monomer concentrations at time zero and time t, respectively, and t is the reaction time in minutes.

Polymerization Kinetics.

Figure 7:
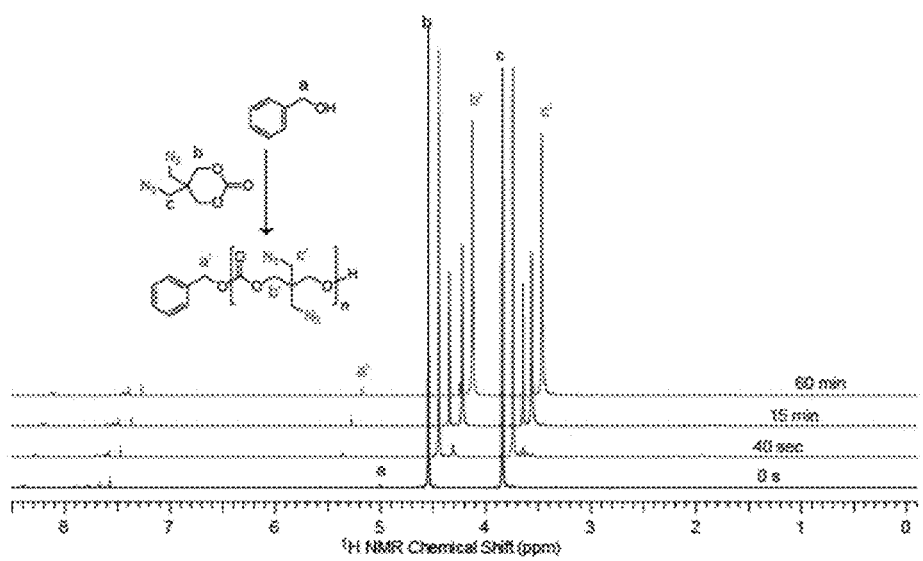
FIG. 7 shows representative $^1$H NMR monitoring of the homopolymerization of AzDXO in CDCl$_3$ at room temperature using benzyl alcohol (Bz) as the initiator and 0.01M DBU as the catalyst.

ROP of AzDXO was carried out at room temperature in chloroform with DBU (0.01M) as the catalyst. The polymerization kinetics was studied using benzyl alcohol (Bz) as an initiator (FIG. 1a) and monitored by gel permeation chromatography (GPC) and $^1$H NMR spectroscopy. The polymerization occurred instantly upon the addition of DBU, as supported by the decrease of the intensity of the GPC signal of the monomer (at 19.35 min) and the appearance of a new, earlier-eluting peak (around 18.10 min) as early as at 20 sec (FIG. 1b). The polymerization was almost completed by 60 min as supported by the disappearance of the monomer peak. $^1$H NMR monitoring (FIG. 7) revealed similar polymerization kinetics. The number-averaged molecular weight ($M_n$) of Bz-P(AzDXO$_n$) determined from GPC exhibited a linear positive correlation with the monomer conversion, with the low polydispersity index (PDI<1.1) maintained as the $M_n$ increased (FIG. 1c), supporting that the initiating sites remained active during the polymerization. The minimal increase of PDI at very high conversion (PDI still well below 1.1) was likely due to decreased solubility of the higher molecular weight active species and led to some chain termination. It was previously shown that under the catalysis of DBU, cyclic carbonate and lactone could be polymerized in controlled/"living" anionic ROP, with a presumed hydrogen-bonding interaction between the initiating alcohol and the nucleophilic nitrogen of DBU. (Endo, et al. *Macromolecules* 2005, 38, 8177; Kiesewetter, et al. *Macromolecules* 2010, 43, 2093.) Our results indicate that the ROP of AzDXO proceeded in a similar fashion. The plot of ln([M]$_0$/[M]) versus time revealed a linear first-order polymerization kinetics (FIG. 1d), indicating that the concentration of the growing end remained constant during polymerization and further supporting the living polymerization mechanism. The ROP rate constants of AzDXO and L-lactide (L-LA) under identical reaction conditions were determined as 0.084 min$^{-1}$ and 0.116 min$^{-1}$, respectively. The similar rate constants make it possible to prepare copolymers of L-LA and AzDXO in a controlled manner without further changing the polymerization conditions.

Thermal Properties of Homopolymers.

Figure 2:
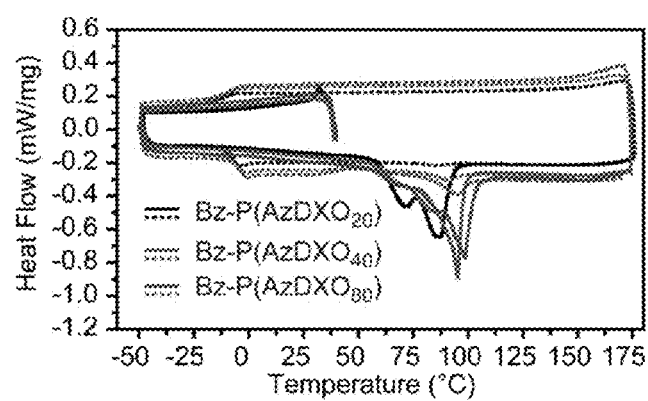
FIG. 2 shows the differential scanning calorimetry of homopolymers of AzDXO with different molecular weights.

The thermal properties of homopolymer Bz-P(AzDXO$_n$) (n=20, 40 or 80) were analyzed by differential scanning calorimetry (DSC). All homopolymers exhibited large endothermic melting peaks around 50-100° C. (FIG. 2), with melting point ($T_m$) increased from 86.31 to 98.43° C. while melting enthalpy (ΔH) remained constant around −52.0 J/g as the chain length increased from 20 to 80 repeating units (Table 1). After quenching the melts to −50° C., a glass transition slightly below 0° C. was detected from the second heating scan in all homopolymers, with the $T_g$ slightly increasing as the chain length increased. In comparison, the most studied aliphatic polycarbonate poly(trimethylene carbonate) of comparable molecular weights exhibited $T_g$'s ranging from −26 to −15° C., a $T_m$ of 36° C. and ΔH$_m$'s of −4.5 to 10 J/g. (Zhu, et al. *Macromolecules* 1991, 24, 1736.) FIG. 2 shows differential scanning calorimetry of homopolymers of AzDXO with different molecular weights. The solid and dotted curves denote the first and the second DSC cycles, respectively.

TABLE 1

Homopolymers of AzDXO and their thermal properties

| Name | AzDXO:BA | $M_n^a$ | PDI$^a$ | $T_m$ (° C.)$^b$ | ΔH (J/g)$^b$ | $T_g$ (° C.)$^c$ |
|---|---|---|---|---|---|---|
| Bz-P(AzDXO)$_{20}$ | 20:1 | 5245 | 1.1512 | 86.31 | −52.49 | −5.1 |
| Bz-P(AzDXO)$_{40}$ | 40:1 | 8546 | 1.0833 | 95.21 | −53.16 | −2.4 |
| Bz-P(AzDXO)$_{80}$ | 80:1 | 14886 | 1.0626 | 98.43 | −51.93 | −1.7 |

$^a$Measured by GPC (THF, 0.3 mL/min, rt), calibrated by polystyrene standards
$^b$Determined from the endothermic peak maximum in the first heating cycle of the DSC scans
$^c$Determined from the midpoint of the first endothermic transition in the second heating cycle of the DSC scans Copolymerization of AzDXO and L-LA.

Figure 3:
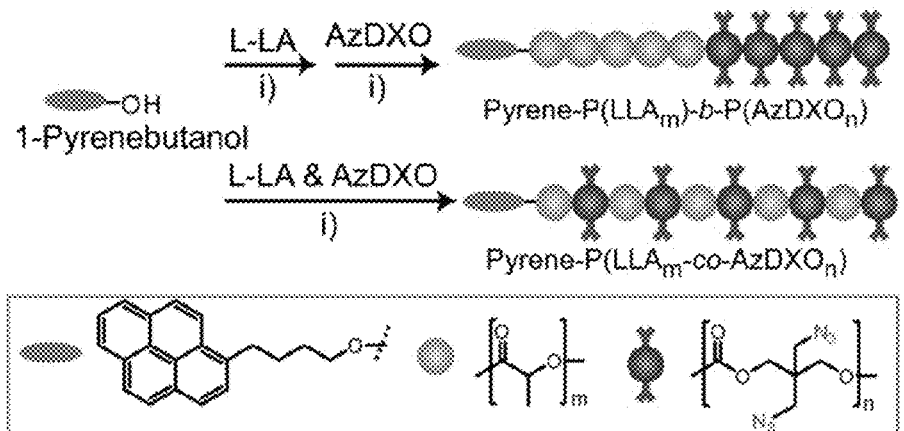
FIG. 3 shows the preparation of block and random copolymers of L-Lactide (L-LA) and AzDXO by sequential and one-pot polymerization, respectively. i) 0.01M DBU, CHCl$_3$, rt.

The comparable DBU-catalyzed homopolymerization rates observed with AzDXO and L-LA make the preparation of copolymers of AzDXO and L-LA straightforward. Using ethylene glycol as an initiator, random copolymers with varying compositions and narrow PDI (~1.1, Table 2) were successfully prepared by simultaneous addition of the two monomers (FIG. 3).

Figure 8:
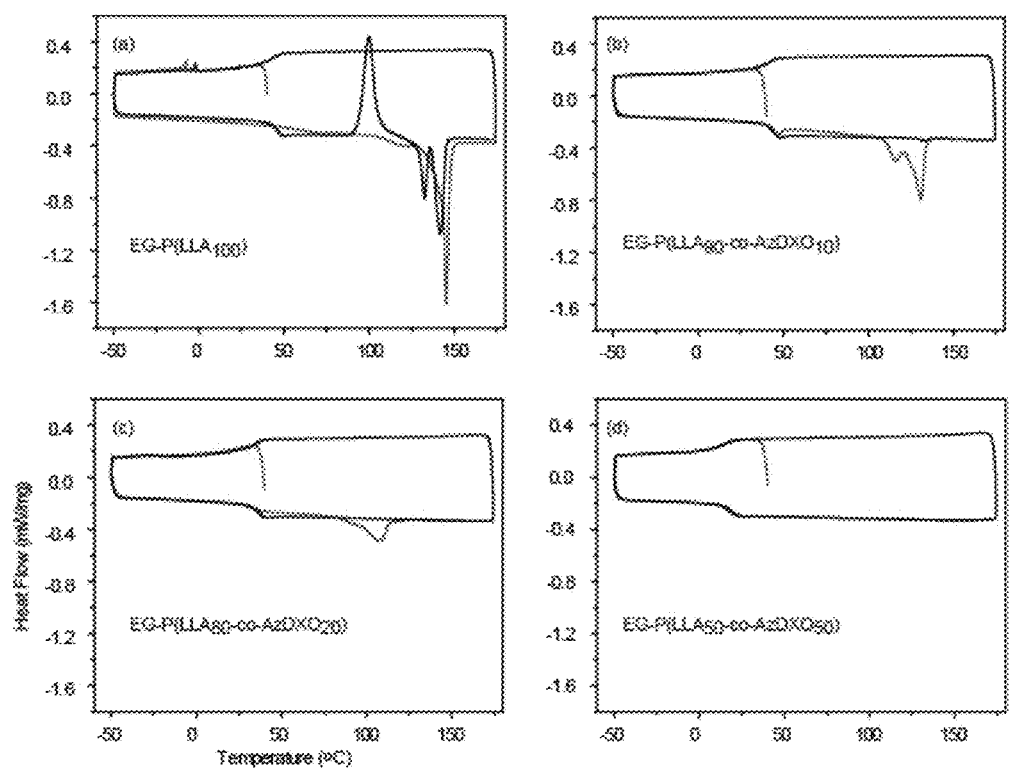
FIG. 8 shows representative DSC scans of random copolymers of AzDXO and L-Lactide with different compositions.

By changing the monomer feed ratios during the one-pot random copolymerization, materials with altered crystallinity and thermal properties could be prepared. The $T_m$'s and ΔH$_m$'s of the random copolymers decreased with the increase of AzDXO content (FIG. 8, Table 2) while their physical appearance changed from crystalline white powders to semi-crystalline translucent solids to amorphous transparent resins. Although homopolymers EG-P(LLA$_{100}$) and EG-P(AzDXO$_{100}$) are both highly crystalline materials with a ΔH of −50.0 J/g and −47.8 J/g, respectively, their equal molar ratio random copolymer EG-P(LLA$_{50}$-co-AzDXO$_{50}$) was amorphous as indicated by the lack of melting peaks (FIG. 8d), supporting a random distribution of AzDXO and L-LA along the copolymer chains.

TABLE 2

Random Copolymers of AzDXO with L-Lactide and their thermal properties

| Name | L-LA:AzDXO:EG | L-LA:AzDXO[a] | $M_n$[b] | PDI[b] | $T_m$ (°C.)[c] | $\Delta H$ (J/g)[c] | $T_g$ (°C.)[d] |
|---|---|---|---|---|---|---|---|
| EG-P(LLA$_{100}$) | 100:0:1 | N.A. | 21299 | 1.11 | 145.5 | −47.8 | 47.2 |
| EG-P(LLA$_{95}$-co-AzDXO$_5$) | 95:5:1 | 95:5.0 | 18727 | 1.12 | 137.3 | −35.3 | 48.1 |
| EG-P(LLA$_{90}$-co-AzDXO$_{10}$) | 90:10:1 | 90:9.8 | 22480 | 1.10 | 130.9 | −28.4 | 45.0 |
| EG-P(LLA$_{80}$-co-AzDXO$_{20}$) | 80:20:1 | 80:20.8 | 22652 | 1.11 | 107.8 | −17.1 | 37.1 |
| EG-P(LLA$_{50}$-co-AzDXO$_{50}$) | 50:50:1 | 50:52.5 | 21157 | 1.11 | N.A. | 0 | 18.2 |

[a]Based on the $^1$H NMR integrations assuming that the L-lactide units were incorporated at theoretical values.
[b]Measured by GPC (THF, 0.3 mL/min, rt), calibrated by polystyrene standards.
[c]Determined from the endothermic peak maximum in the first heating cycle of the DSC scans.
[d]Determined from the midpoint of the first endothermic transition in the second heating cycle of the DSC scans.

Block copolymers tethered by two or more distinct chain segments can exhibit unique properties distinctive from those of the corresponding homopolymers and random copolymers. (Hadjichristidis, et al. *Block copolymers: synthetic strategies, physical properties, and applications*; John Wiley and Sons, 2002.) Block copolymers can be prepared by sequentially growing the blocks using different polymerization techniques following proper end-group manipulations. (Hedrick, et al. *Macromolecules* 1998, 31, 8691; Feng, et al. *Macromolecules* 2002, 35, 2084; Hawker, et al. *Macromolecules* 1998, 31, 213; Matyjaszewski, K. *Macromol. Symp.* 1998, 132, 85.) Alternatively, they can be prepared using the same polymerization technique (e.g. Atom Transfer Radical Polymerization and Reversible Addition-Fragmentation Chain Transfer Polymerization) under identical reaction conditions by feeding monomers of interest in batches. (Matyjaszewski, et al. *Chem. Rev.* 2001, 101, 2921; Chong, et al. *Macromolecules* 1999, 32, 2071.) The latter strategy eliminates the need for end group functionalization and is potentially far more efficient during scale-ups. The incompatibility of many organic functional groups with ROP conditions, however, has made it difficult to broadly apply such a strategy to the preparation of functional biodegradable block copolymers. Compatible with ROP conditions and with a ROP rate constant comparable to that of L-LA, AzDXO offers a unique opportunity to the efficient preparation of functional poly(ester-carbonate) block copolymers.

Block copolymer Pyrene-P(LLA$_x$)-b-P(AzDXO$_y$) was prepared with fixed L-LA block length (x=100) and varying AzDXO block lengths (y=5, 10, 20, 35) by DBU-catalyzed ROP at room temperature using 1-pyrenebutanol as the initiator. 1-Pyrenebutanol was chosen for easy monitoring of the polymerization by GPC and NMR due to its strong UV-vis absorption and distinct down-field $^1$H NMR signals away from those of the polymeric units. The rapid polymerization (<1 h) and high conversion of monomers (>99%) under the employed conditions enabled the sequential feed of monomers without the need for purification of the first polymer block. All block copolymers were prepared in quantitative yield with narrow polydispersity (Table 3).

TABLE 3

Block and random copolymers of L-LA and AzDXO

| Name[a] | L-LA:AzDXO[b] | $M_n$[c] | PDI[c] |
|---|---|---|---|
| Pyrene-P(LLA$_{100}$) | 97.0:0 | 19392 | 1.06 |
| Pyrene-P(LLA$_{100}$)-b-P(AzDXO$_5$) | 116.6:3.2 | 22356 | 1.06 |
| Pyrene-P(LLA$_{100}$)-b-P(AzDXO$_{10}$) | 106.8:9.2 | 23487 | 1.06 |
| Pyrene-P(LLA$_{100}$)-b-P(AzDXO$_{20}$) | 110.8:18.3 | 27362 | 1.11 |
| Pyrene-P(LLA$_{100}$)-b-P(AzDXO35) | 98.8:33.1 | 31030 | 1.07 |
| Pyrene-P(AzDXO$_{100}$) | 0:106.0 | 19888 | 1.14 |
| Pyrene-P(LLA$_{100}$-co-AzDXO$_{20}$)[d] | 98.0:18.6 | 25524 | 1.07 |

[a]The naming of the samples reflect the theoretical copolymer compositions;
[b]copolymer compositions determined from $^1$H NMR;
[c]number-averaged molecular weight and polydispersity index determined from GPC using an ELS detector;
[d]two monomers were added in one-step for the preparation of random copolymer.

Figure 9:
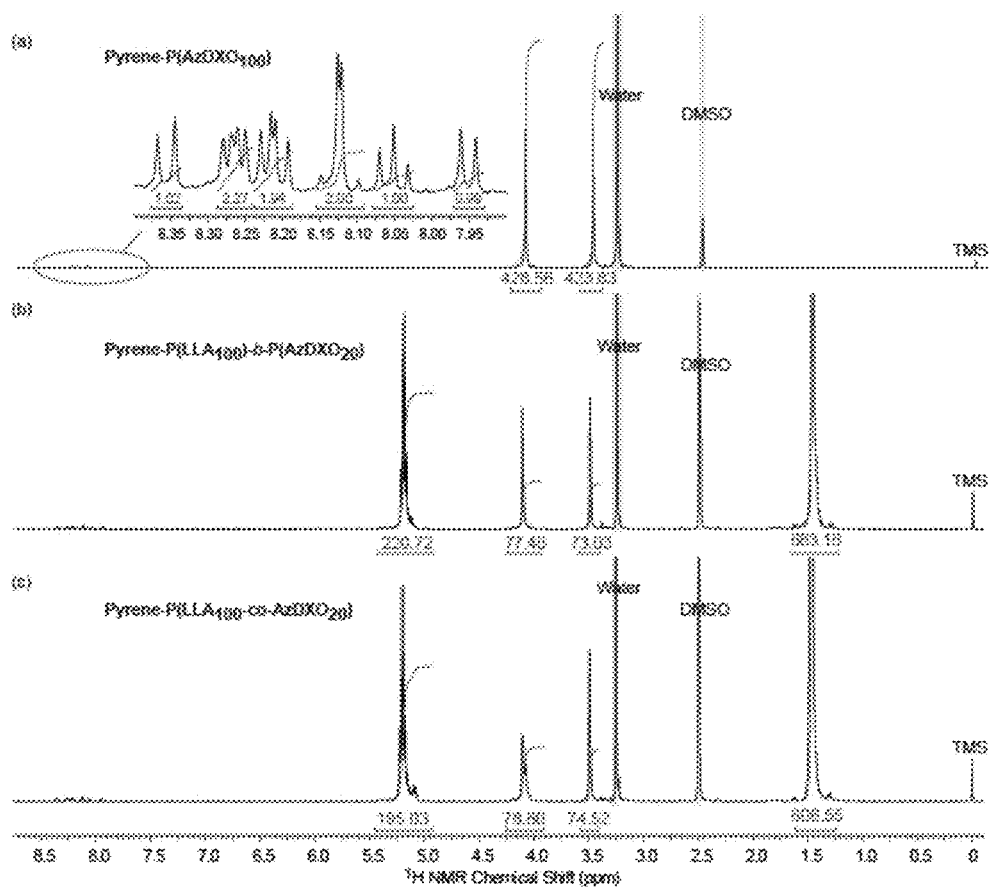
FIG. 9 shows representative $^1$H NMR spectra of (a) homopolymer Pyrene-P(AzDXO$_{100}$), (b) block copolymer Pyrene-P(LLA$_{100}$)-b-P(AzDXO$_{20}$), and (c) random copolymer Pyrene-P(LLA$_{100}$-co-AzDXO$_{20}$).
Figure 10:
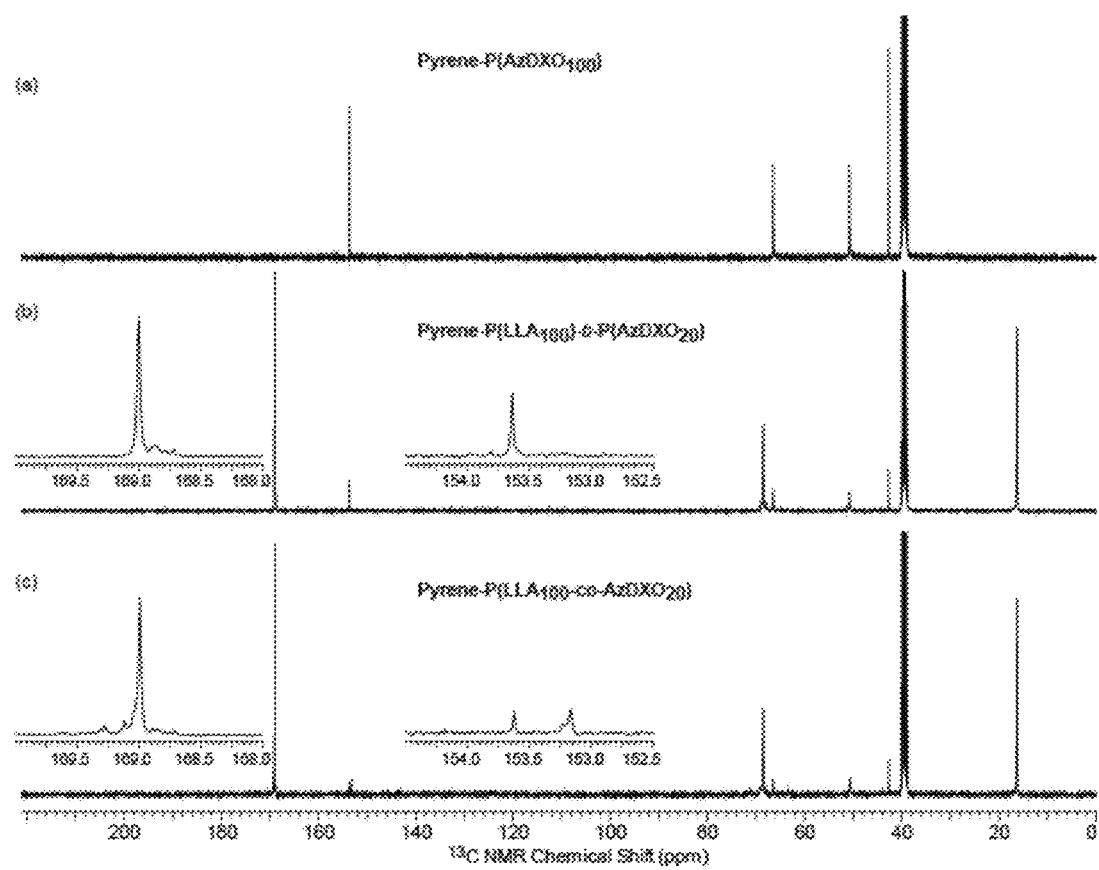
FIG. 10 shows representative $^{13}$C NMR spectra of (a) homopolymer Pyrene-P(AzDXO$_{100}$), (b) block copolymer Pyrene-P(LLA$_{100}$)-b-P(AzDXO$_{20}$), and (c) random copolymer Pyrene-P(LLA$_{100}$-co-AzDXO$_{20}$).
Figure 11:
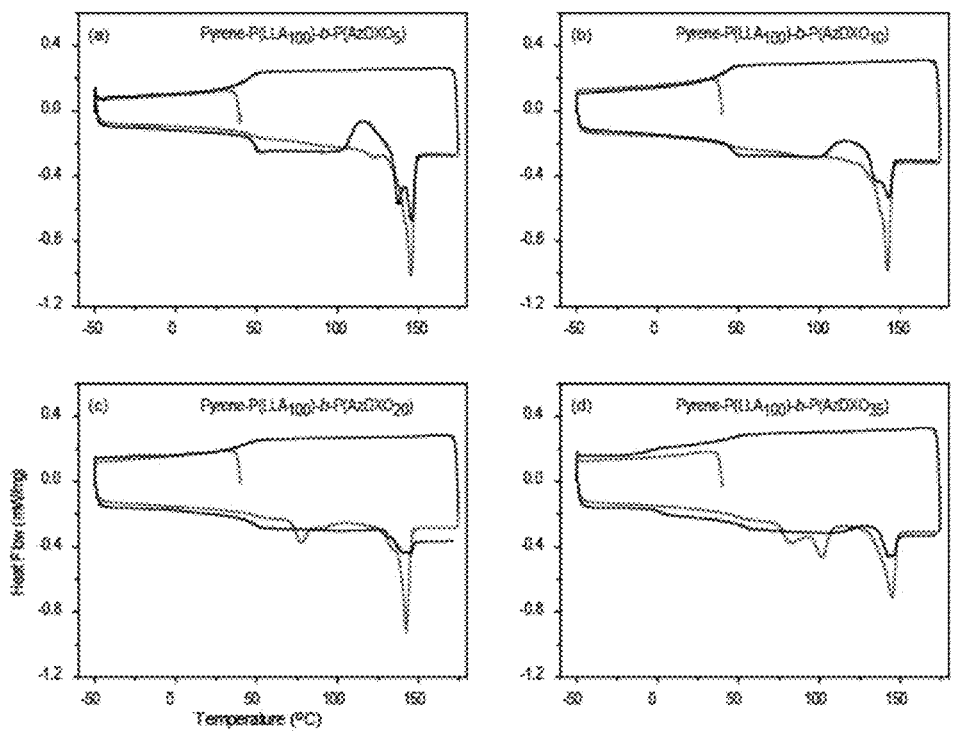
FIG. 11 shows representative DSC scans of block copolymers with fixed L-lactide block length but varying AzDXO block lengths.

Representative GPC traces for Pyrene-P(LLA$_{100}$) and Pyrene-P(LLA$_{100}$)-b-P(AzDXO$_{35}$) (FIG. 4a) show that both ELS and UV-vis peaks shifted to an earlier elution upon feeding the second monomer AzDXO while the peak shapes remained unchanged. The drop in intensity of UV-vis signal upon the polymerization of the P(AzDXO$_{35}$) block supports that the polymerization of AzDXO was initiated by the Pyrene-P(LLA$_{100}$) block. $^1$H and $^{13}$C NMR (FIGS. 9 and 10) showed two distinct groups of peaks correlating to the two functional blocks in the block copolymer whereas broader and more scattered peaks for the random copolymer. The microstructural difference of the copolymers also translated into distinctive thermal properties. As the AzDXO block grew longer after the L-LA block, the appearance of two distinct melting peaks and two distinct glass transitions in the block copolymer became apparent (FIG. 11). For instance, Pyrene-P(LLA$_{100}$)-b-P(AzDXO$_{20}$) exhibited two melting peaks ($T_m^1$=80.6° C.; $T_m^2$=143.6° C.) and two glass transitions ($T_g^1$=−1.5° C.; $T_g^2$=48.7° C.) that resembled the respective transitions for the homopolymers Pyrene-P(LLA$_{100}$) and P(AzDXO$_{100}$) (FIG. 4b), supporting the block microstructure. By contrast, the random copolymer Pyrene-P(LLA$_{100}$-co-AzDXO$_{20}$) only exhibited one small broad melting peak around 117.8° C. and a single glass transition around 39.2° C., consistent with its more randomly distributed compositions and less ordered microstructure.

Figure 4:
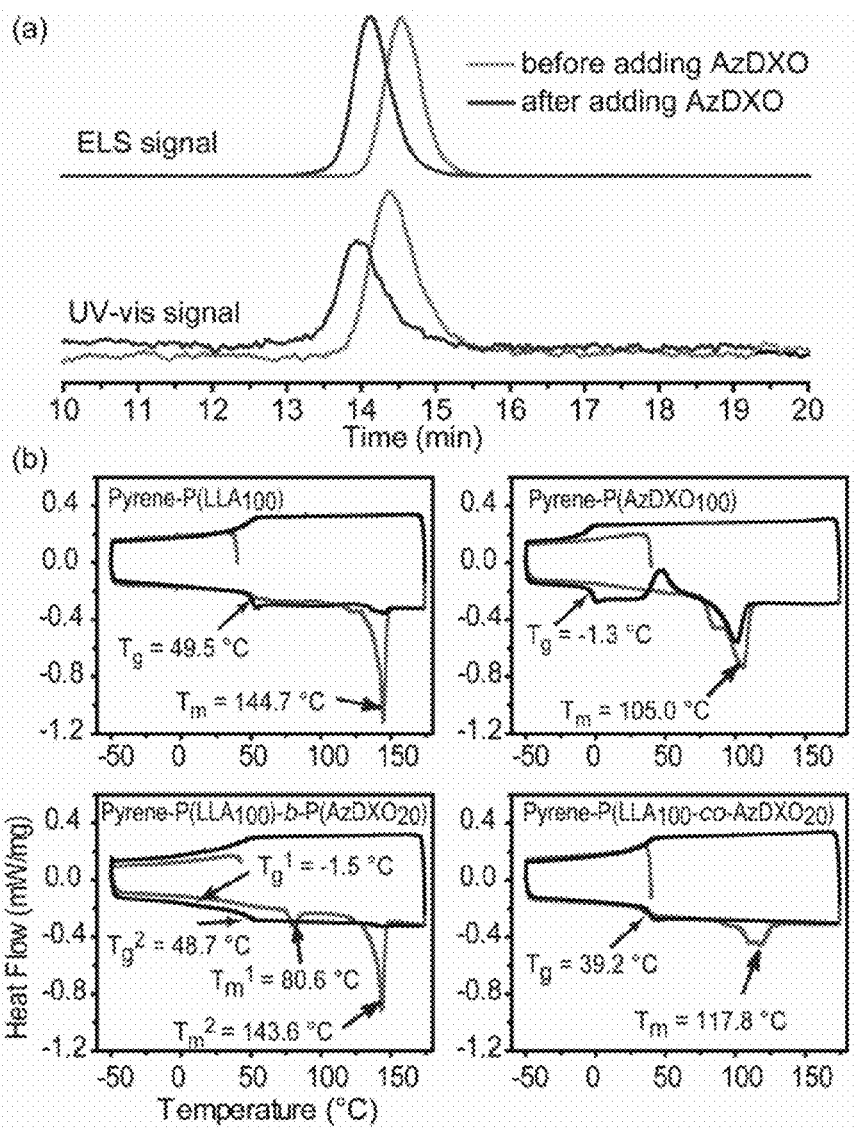
FIG. 4 shows GPC traces and DSC scans confirming the successful preparation of block and random copolymers of L-LA and AzDXO.

FIG. 4 shows GPC traces and DSC scans confirming the successful preparation of block and random copolymers of L-LA and AzDXO. (a) Representative GPC traces for Pyrene-P(LLA$_{100}$)-b-P(AzDXO$_{35}$) before and after feeding AzDXO; (b) DSC curves of homopolymers, and block and random copolymers of L-LA and AzDXO.

Functionalization of Block Copolymers Via Copper-Catalyzed Azido-Alkyne Cycloaddition (CuAAC).

Figure 12:
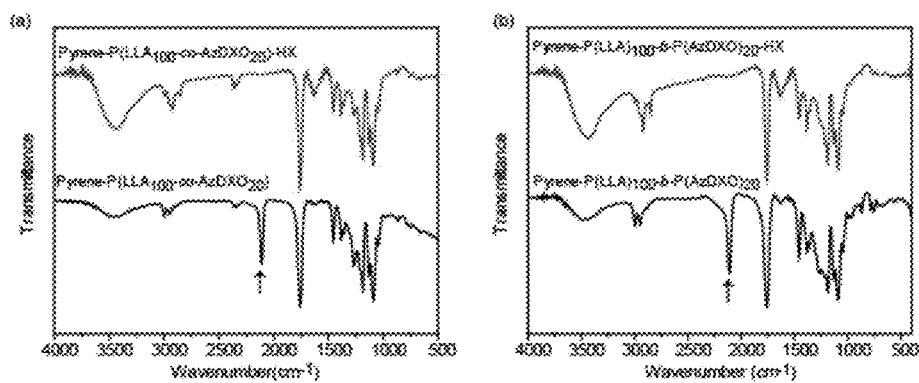
FIG. 12 shows representative FTIR spectra of random and block copolymers before and after modification using 5-hexyn-1-ol (HX) through CuAAC supported quantitative reaction.
Figure 13:
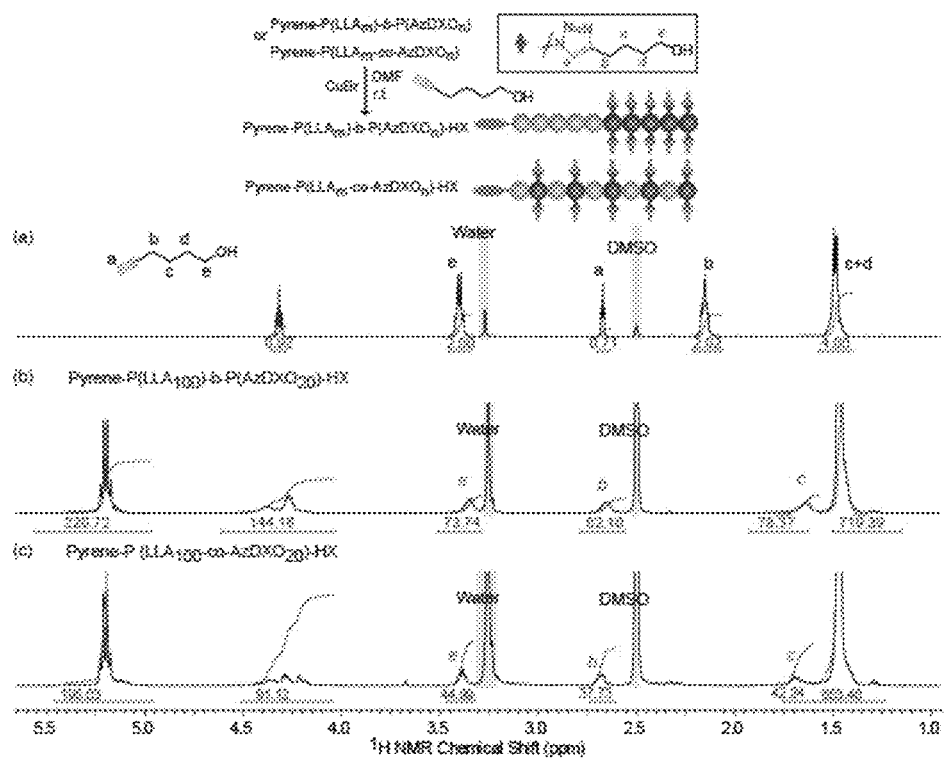
FIG. 13 shows representative $^1$H NMR spectra confirming the successful attachment of 5-hexyn-1-ol (HX) (a) to the block copolymer Pyrene-P(LLA$_{100}$)-b-P(AzDXO$_{20}$)-HX (b) and the random copolymer Pyrene-P(LLA$_{100}$-co-AzDXO$_{20}$)-HX (c).

To demonstrate the facile post-polymerization conversions of the azido functionality, copper-catalyzed azido-alkyne cycloaddition (CuAAC) reaction was carried out at room temperature in DMF to attach 5-hexyn-1-ol (HX) to the block and random copolymers (FIG. 5a). (Kolb, et al. *Angew. Chem.*, Int. Ed. 2001, 40, 2004; Hawker, et al. *Aust. J. Chem.* 2007, 60, 381.) Nearly all azido groups were converted by 24 h, as supported by FTIR (FIG. 12) and 1H NMR spectra (FIG. 13). The GPC traces, however, revealed complex elution profiles for HX-modified block and random copolymers (FIG. 5b&c). The apparent $M_n$ calculated from the main peaks showed lower value than the original polymers, indicating the decrease of hydrodynamic radii of the polymers upon CuAAC, likely as a result of the collapse of the hydrophilic HX side chains due to either poor solvation or complexation with residue $Cu^{2+}$ (Jiang, et al. *Macromolecules* 2008, 41, 1937.) The extra shoulder peaks at earlier elution time may have derived from copolymer aggregates formed via the triazole-$Cu^2$ complexation. After intensive dialysis against $Cu^{2+}$ sequestrant 2,2'-bipyridine, these shoulder peaks was reduced although never completely removed.

Figure 5:
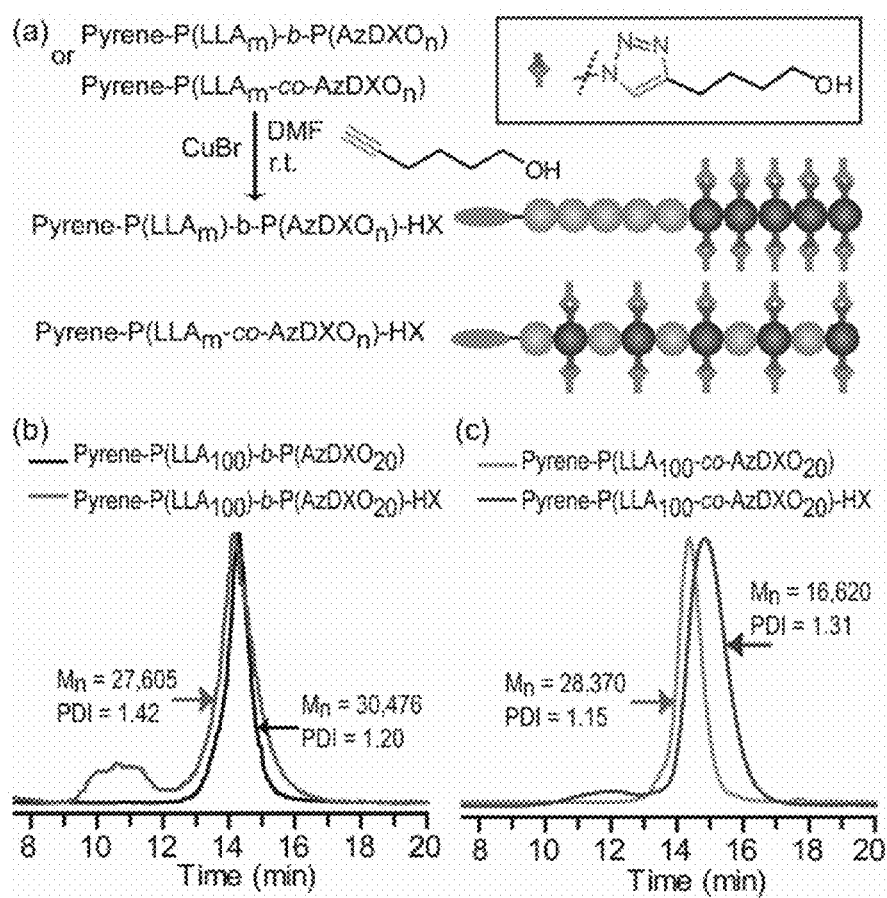
FIG. 5 shows the functionalization of block and random copolymers with 5-hexyn-1-ol (HX) via copper-catalyzed azido-alkyne cycloaddition (CuAAC).

FIG. 5 shows functionalization of block and random copolymers with 5-hexyn-1-ol (HX) via copper-catalyzed azido-alkyne cycloaddition (CuAAC). (a) Reaction scheme; (b) GPC traces (DMF, 50° C.), $M_n$ and PDI of block copolymer P(LLA$_{100}$)-b-P(AzDXO$_{20}$) before and after CuAAC; (c) GPC traces (DMF, 50° C.), $M_n$ and PDI of random copolymer P(LLA$_{100}$)-co-P(AzDXO$_{20}$) before and after CuAAC.

Functionalization of Block Copolymers Via Strain-Promoted Azido-Alkyne Cyclcoaddition (SPAAC).

To avoid the potential toxicity of residual copper catalyst in CuAAC, copper-free, strain-promoted azido-alkyne cyclcoaddition (SPAAC) was carried out to modify the block and random copolymers (FIG. 6a) using aza-dibenzocyclooctyne NHS ester (DBCO-NHS). (Baskin, et al. *Aldrichimica Acta* 2010, 43, 15; Agard, et al. *J. Am. Chem. Soc.* 2005, 127, 11196.) Near complete conversion (>95%) of azido groups was achieved in 4 h when 1 eq. DBCO-NHS was added in DMF. Complete conversion was achieved when the DBCO-NHS to azide ratio was increased by 3 folds. GPC traces revealed the expected increase of molecular weight upon the modification of either block (FIG. 6b) or random copolymer (FIG. 6c) with the narrow polydispersity retained. $^1$H NMR (FIG. 6d) confirmed the complete disappearance of proton resonance for —CH$_2$N$_3$ at 3.50 ppm (FIG. 9) and the appearance of proton resonances associated with the covalently attached DBCO-NHS. The resonance around 4.40 ppm corresponding to the AzDXO unit was more readily detected in Pyrene-P(LLA$_{100}$-co-AzDXO$_{20}$)-DN than in Pyrene-P(LLA$_{100}$-b-AzDXO$_{20}$)-DN, supporting the random distribution of the bulky DN rings and consequently the less profound shielding effect in the former. Consistent with this observation, higher peak intensities were also detected for the resonances corresponding to the LLA protons in the random copolymers.

Figure 6:
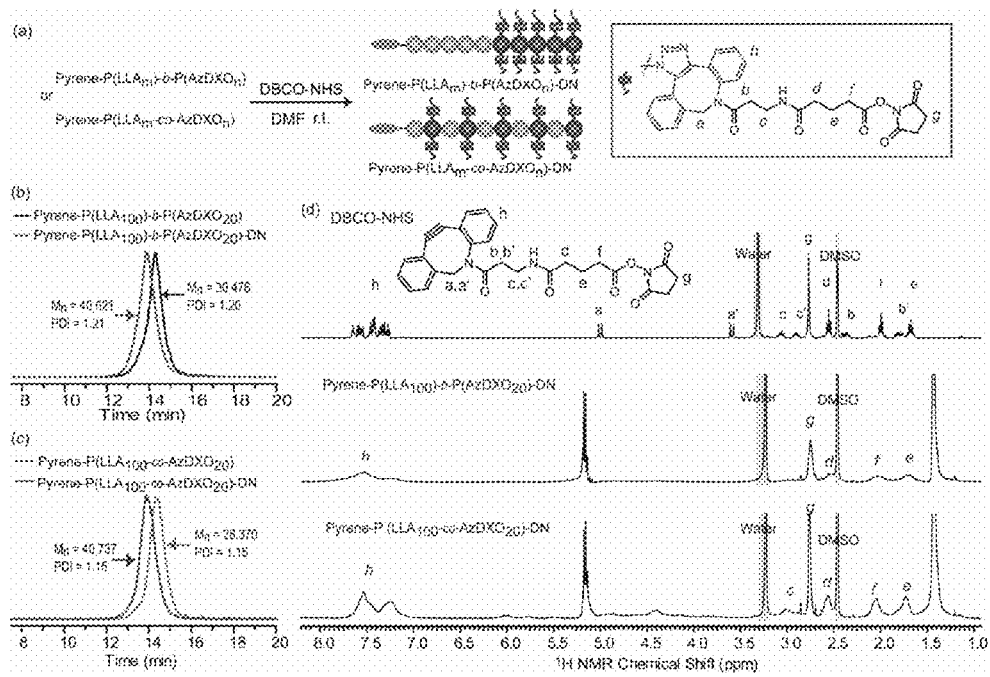
FIG. 6 shows representative GPC traces and $^1$H NMR spectra indicating the successful modification of block and random copolymers by strain-promoted azido-alkyne cycloaddition (SPAAC).

FIG. 6 shows GPC traces and $^1$H NMR spectra indicated the successful modification of block and random copolymers by strain-promoted azido-alkyne cycloaddition (SPAAC). (a) reaction scheme; (b) GPC traces (ELS detector) of block copolymer Pyrene-P(LLA$_{100}$)-b-P(AzDXO$_{20}$) before and after SPAAC; (c) GPC traces (ELS detector) of random copolymer Pyrene-P(LLA$_{100}$-co-AzDXO$_{20}$) before and after SPAAC; (d) $^1$H NMR of DBCO-NHS (DN) (top), Pyrene-P (LLA$_{100}$)-b-P(AzDXO$_{20}$)-DN (middle) and Pyrene-P (LLA$_{100}$-co-AzDXO$_{20}$)-DN (bottom).

Experimental Section

Materials and Instrumentation:

Aza-dibenzocyclooctyne NHS ester (DBCO-NHS) was purchased from Click Chemistry Tools Inc. (Macon, Ga., USA). All other chemicals were purchased from Sigma-Aldrich (St. Louis, Mo.) and used as received unless otherwise specified. Chloroform and deuterated chloroform used for reactions were pre-dried by refluxing with phosphorus pentoxide overnight and then distilled under argon. Triethyl amine (TEA, >99%) was dried by refluxing with calcium hydride and distilled under argon. (3S)-Cis-3,6-dimethyl-1, 4-dioxane-2,5-dione (L-lactide, 98%) was further purified prior to use by repeated (3×) recrystallization from anhydrous toluene. 1,8-Diazabicyclo[5.4.0]-undec-7-ene (DBU, 98%) was freshly distilled under vacuum prior to use.

$^1$H (400 MHz) and $^{13}$C NMR (100 MHz) spectra were recorded on a Varian INOVA-400 spectrometer in deuterated chloroform (CDCl$_3$, 99.8 atom % D with 0.03% v/v TMS) or dimethyl sulfoxide-d6 (99.9 atom % D with 0.03% v/v TMS). High resolution mass spectroscopy (HRMS) spectra were recorded on a Waters Q-T of Premier mass spectrometer using electro spray ionization (ESI) with W-mode and a spray voltage of 3500V. Samples (0.1 or 10 mg/mL) in methanol or methanol/water mixture (50:50) were infused at a rate of 5 μl/min. Fourier transformed infrared spectroscopy (FTIR) spectra were taken on a Thermo Electron Nicolet IR100 spectrometer with 2-cm$^{-1}$ spectral resolution. Liquid samples were coated on a NaCl salt window and solid samples were mold-pressed into thin transparent discs with KBr, respectively.

Gel permeation chromatrography (GPC) measurements were taken on a Varian Prostar HPLC system equipped with two 5-mm PLGel MiniMIX-D columns (Polymer Laboratory, Amherst, Mass.), a UV-vis detector and a PL-ELS2100 evaporative light scattering detector (Polymer Laboratory, Amherst, Mass.). For characterization of azido-functionalized polycarbonates and poly(ester-carbonates), THF was used as an eluent at a flow rate of 0.3 mL/min at rt. The number-averaged molecular weight ($M_n$) and the polydispersity index (PDI) were calculated by a Cirrus AIA GPC Software using narrowly dispersed polystyrenes (ReadyCal kits, PSS Polymer Standards Service Inc. Germany) as calibration standards. For characterization of the more polar functional polymers following "click" chemistry, DMF was used as an eluent at a flow rate of 0.3 ml/min at 50° C. The $M_n$ and PDI were calculated by using narrowly dispersed poly(methyl methacrylates) (EasiVial, Polymer Laboratory, Amherst, Mass.) as standards.

The thermal properties of polymers were determined on a TA Instruments Q200 Differential Scanning calorimeter (DSC). The enthalpy (cell constant) and temperatures are calibrated by running a high-purity indium standard under the conditions identical to those used for sample measurements. To determine the crystallinity and glass transitions of the polymer samples, each specimen (around 5 mg) was subject to two scanning cycles: (1) cooling from 40° C. (standby temperature) to −50° C. at −10° C./min, equilibrating for 2 min before being heated to 175° C. at a heating rate of 10° C./min; (2) cooling to −50° C. at −10° C./min, equilibrating for 2 min, and then being heated to 175° C. at a rate of 10° C./min. The endothermic peak maximum in the first heating cycle was recorded as the melting temperature ($T_m$), and its associated peak integration was calculated as melting Monomer Synthesis and Polymerizations 2,2-bis(azidomethyl)propane-1,3-diol 2,2-Bis(bromomethyl)propane-1,3-diol (98%, 104.7 g, 0.40 mol) was dissolved in DMSO (300 mL) in a 1000-mL 3-neck flack equipped with a reflux condenser, to which sodium azide (65.0 g, 1.0 mol) was added under argon. The suspension was heated to 110° C. and stirred for 16 h. After being cooled to rt, 150-mL water was added and the mixture was transferred to a 2-L separatory funnel and extracted with 800-mL ethyl acetate 3 times. The combined organic phase was washed by 200-mL saturated brine 3 times and dried with sodium sulfate. Pale yellow oil (71.0 g, 95.3% yield) was obtained after removing the volatiles under vacuum. $^1$H NMR (CDCl$_3$, 400 MHz, 20° C.): δ 3.629-3.616 (d, 4H, J=5.1 Hz), 3.420 (s, 4H), 2.473-2.446 (t, 2H, J=5.1 Hz) ppm. $^{13}$C NMR (CDCl$_3$, 100 MHz, 20° C.): δ 63.841, 51.907, 45.020 ppm. ESI-HRMS (m/z): C$_5$H$_{10}$N$_6$O$_2$Na$^+$ [M+Na]$^+$, calculated 209.0763. found 209.0754.

5,5-bis(azidomethyl)-1,3-dioxane-2-one (AzDXO)

To a solution of ethyl chloroformate (97%, 47.8 g, 0.44 mol) in anhydrous THF (300 mL) was added a THF solution (40 mL) of 2,2-bis(azidomethyl)propane-1,3-diol (34.0 g, 0.18 mol) over 10 min at 0° C. under argon. Dry TEA (50.0 g, 0.50 mol) was added slowly over 30 min. The reaction was continued in ice bath for 4 h and then at rt overnight. After removing the white precipitate by filtration, the volatile was removed under vacuum. The crude product was dissolved in dichloromethane and passed through a short silica gel pad (230-400 mesh size) to remove salts. After removing the solvent by rotovapping, ethyl ether (250 mL) was added to dissolve the product and refluxed for 10 min. Upon cooling, crystalline solid product was collected by filtration. The recrystallization was repeated once. After dried under vacuum for 48 h, spectroscopically pure product (18.3 g) was obtained in 47.9% yield. $^1$H NMR (CDCl$_3$, 400 MHz, 20° C.): δ 4.251 (s, 4H), 3.550 (s, 4H) ppm. 13C NMR (CDCl$_3$, 100 MHz, 20° C.): δ 147.33, 70.41, 50.34, 36.61 ppm. $^1$H NMR (DMSO-D6, 400 MHz, 40° C.): δ 3.59 (s, 4H) 4.27 (s, 4H) ppm; $^{13}$C NMR (DMSO-D6, 100 MHz, 40° C.): δ 147.94, 70.90, 51.20, 36.87 ppm. ESI-HRMS (m/z): C$_6$H$_8$N$_6$O$_3$Na$^+$ [M+Na]$^+$, calculated 235.0556. found 235.0556.

Typical Procedures for the Homopolymerization of AzDXO.

AzDXO (0.848 g, 4.0 mmol) and 800-μL benzyl alcohol solution (0.1M in chloroform) were mixed in a 6-mL reaction vessel under argon, to which 3.0-mL chloroform was added to completely dissolve the monomer. The polymerization was initiated by the injection of 200-μL DBU solution (0.2 M in chloroform). The reaction was terminated after 2 h by adding benzoic acid (99.5%, 12.2 mg, 0.1 mmol). The polymer was precipitated by 50-mL methanol, redissolved in 4-mL chloroform and reprecipitated in methanol. The precipitation purification was repeated twice to remove residue catalyst and benzoic acid. The final precipitate was further washed by ethyl ether and dried in vacuum oven at 60° C. for at least 48 h prior to any thermal analysis. Around 0.820 g white powder product resulted (97% yield).

Typical Procedures for the Random Copolymerization of AzDXO with L-LA.

L-LA and AzDXO were polymerized in one-pot using CHCl$_3$ as solvent, ethylene glycol (EG) as the initiator, DBU (0.01M) as the catalyst, and with the total monomer concentration kept at 1.0 M. The molar ratio of AzDXO and L-LA was varied to prepare random block copolymers with different AzDXO contents. For example, to prepared EG-F (LLA$_{90}$-co-AzDXO$_{10}$), chemicals at the molar ratio of [L-LA]$_0$:[AzDXO]$_0$:[EG]:[DBU]=90:10:1:0.01 were added. AzDXO (0.085 g, 0.4 mmol), recrystallized L-LA (0.519 g, 3.6 mmol), and 400-μL ethylene glycol solution (0.1 M in chloroform) were mixed in a 6-mL reaction vessel under argon, to which 3.4-mL chloroform was added to completely dissolve the monomer. The polymerization was initiated by the injection of 200-μL DBU solution (0.2 M in chloroform). The reaction was terminated after 2 h by adding benzoic acid, and the copolymer EG-P(LLA$_{90}$-co-AzDXO$_{10}$) was purified as described above and resulted in 0.59 g white powder (98% yield).

Typical Procedures for the Sequential Copolymerization of AzDXO with L-LA.

L-LA and AzDXO were polymerized sequentially using CHCl$_3$ as solvent, 1-pyrenbutanol as the initiator, DBU (0.01 M) as the catalyst, and with [L-LA]$_0$=1.0 M. The amount of AzDXO added next was varied to prepare block copolymers with different AzDXO block lengths. For example, to prepared Pyrene-P(LLA$_{100}$)-b-P(AzDXO$_{20}$), chemicals at the molar ratio of [L-LA]$_0$: [AzDXO]$_0$:[1-pyrenebutanol]: [DBU]=100:20:1:0.01 were added in the first step. Rrecrystallized L-LA (0.577 g, 4.0 mmol) and 1-pyrenebutanol (99%, 10.9 mg, 0.040 mmol) were dissolved in 3.8-mL chloroform under argon. The polymerization was initiated by the injection of 200-μL DBU solution (0.2 M in chloroform). After 2 h, AzDXO (0.169 g, 0.80 mmol) was added under argon and reacted for another 2 h before benzoic acid (≥99.5%, 12.2 mg, 0.1 mmol) was added to terminate the polymerization. The product was purified as described above and the copolymer Pyrene-P(LLA$_{100}$)-b-P(AzDXO$_{20}$) was obtained in the white powder form (0.72 g, 97% yield).

Side-Chain Functionalization by "Click" Chemistry:

Typical Procedures for the Functionalization of Poly(Ester-Carbonates) by Copper-Catalyzed Azido-Alkyne Cycloaddition (CuAAC).

The copolymers were functionalized in DMF at rt under inert atmosphere with varying amounts of 5-hexyn-1-ol by CuAAC. For example, Pyrene-P(LLA$_{100}$)-b-(AzDXO$_{20}$) or Pyrene-P(LLA$_{100}$-co-AzDXO$_{20}$) (30.0 mg, ~70 μmol of azido groups) and 5-hexyn-1-ol (96%, 120 mg, 1.23 mmol) were dissolved in 2.0 mL DMF, and degassed with argon for 30 min before CuBr (99.999%, 5 mg) was added. The reaction was allowed to continue at rt for 24 h. The product was transferred to a 4-mL regenerated cellulose dialysis tubing (MWCO=3500 Dalton) and dialyzed against 400-mL DMF in the presence of 0.1-g 2,2'-bipyridine to remove the copper catalyst. The DMF solution was changed every two days for 7 days. After additional dialysis against fresh DMF without 2,2'-bipyridine for another 2 days, the polymer solution in the dialysis tubing was dropped into 50-mL ethyl ether for precipitation. Light green powder (32.0 mg, yield≈88%) was obtained after drying in vacuum oven at rt for 48 h.

Typical Procedures for the Functionalization of Poly(Ester-Carbonates) by Copper-Free Strain-Promoted Azido-Alkyne Cyclcoaddition (SPAAC).

The copolymers were functionalized in DMF at rt with varying amounts of DBCO-NHS by SPAAC. For example, Pyrene-P(LLA$_{100}$)-b-P(AzDXO$_{20}$) or Pyrene-P(LLA$_{100}$-co- AzDXO$_{20}$) (30.0 mg, ~70 μmol of azido groups) and DBCO-NHS (101.0 mg, 210 μmol) were dissolved in 2.0-mL DMF, and reacted at rt for 12 h before being precipitated in 50-mL ethyl ether. The precipitate was redissovled in DMF and reprecipitated in ethyl ether. Off-white powder (~60.0 mg, yield≈93%) was obtained after drying in vacuum oven at rt for 48 h.

Synthesis of Mono Azido-Functional Cyclic Carbonate Monomer

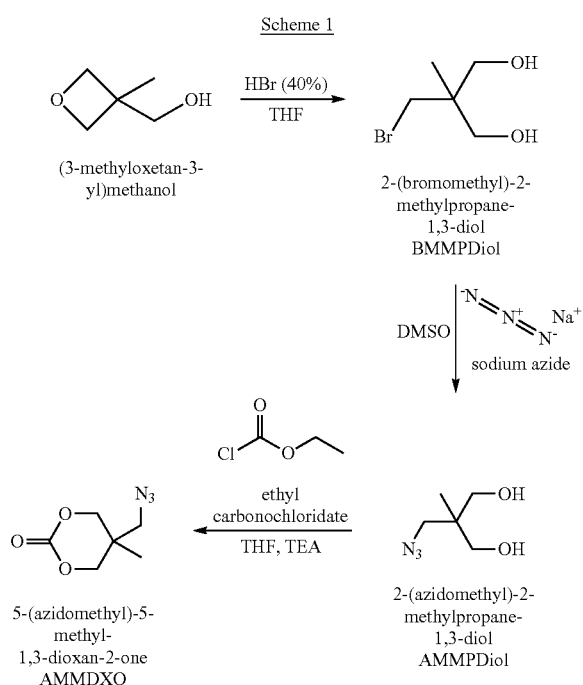

Synthesis of 2-(bromomethyl)-2-methylpropane-1,3-diol (BMMPDiol)

Figure 14:
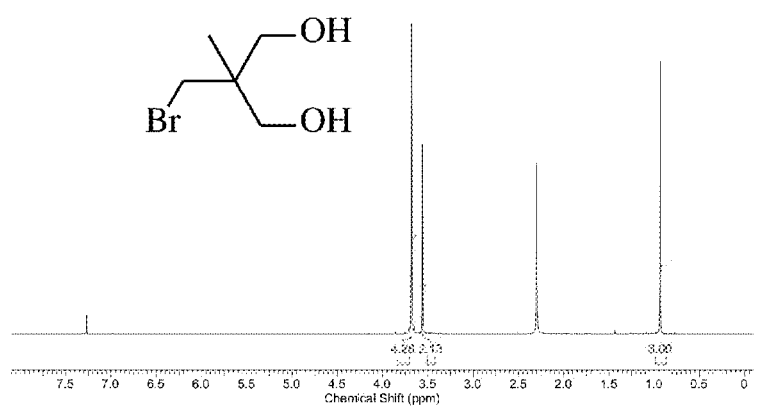
FIG. 14 shows representative $^1$H NMR of 2-(bromomethyl)-2-methylpropane-1,3-diol (BMMPDiol) in CDCl$_3$.
Figure 15:
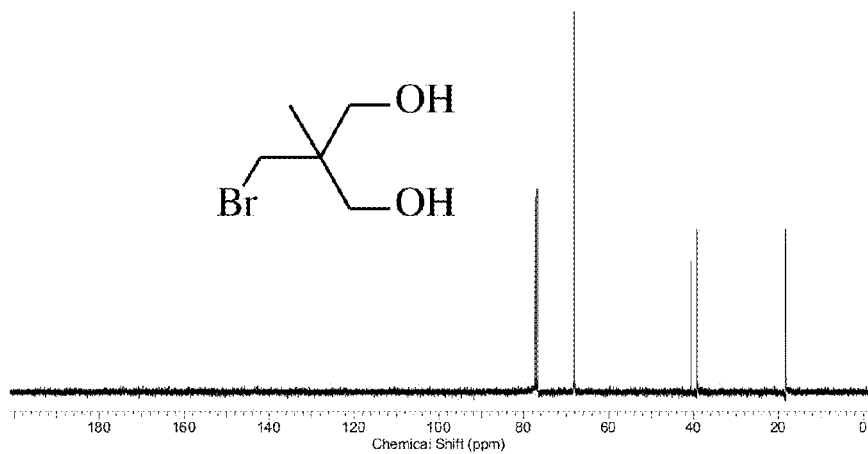
FIG. 15 shows representative $^{13}$C NMR of 2-(bromomethyl)-2-methylpropane-1,3-diol (BMMPDiol) in CDCl$_3$.

Into a 500-mL 3-neck flask equipped with a condenser, a thermometric and argon inlet, 3-methyl-3-oxetanemethanol (20.4 g, 0.20 mol) was dissolved in 250 mL THF and cooled in sodium chloride/ice bath. Aqueous hydrobromic acid (48 wt %, 80 mL) was dropped slowly in 1.5 h. After reacting in salt/ice bath for 4 h and then at room temperature for another 12 h, 150 mL saturated sodium chloride solution was added. The solution was extracted with 250 mL of ethyl ether for 4 times. The combined ether solution was washed with 100 mL of saturated sodium chloride solution twice and then dried over anhydrous sodium sulfate. The solution was filtered and the volatile was removed under vacuum, resulting in white powder (35.0 g, yield=96.1%). $^1$H NMR (FIG. 14) (Chloroform-d, 400 MHz): δ(ppm) 3.68 (s, 4H), 3.56 (s, 2H), 0.93 (s, 3H). $^{13}$C NMR (FIG. 15) (Chloroform-d, 100 MHz): δ (ppm) 68.2, 40.6, 39.2, 18.4.

Synthesis of 2-(azidomethyl)-2-methylpropane-1,3-diol (AMMPDiol)

Figure 16:
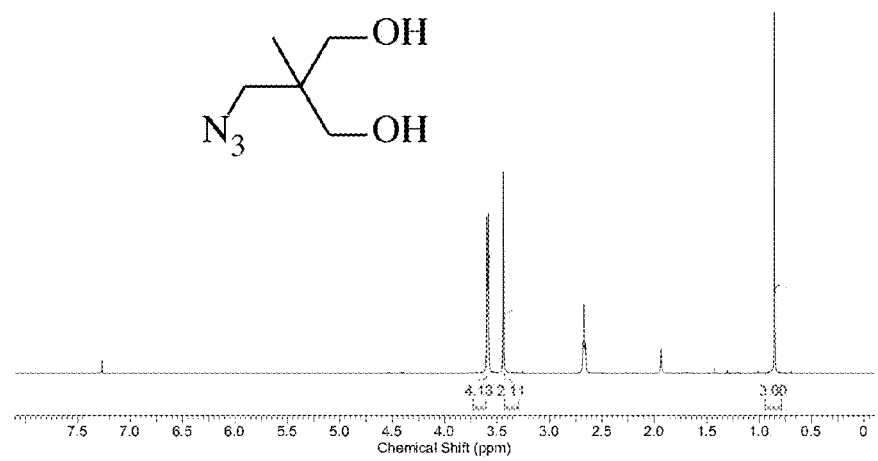
FIG. 16 shows representative $^1$H NMR of 2-(azidomethyl)-2-methylpropane-1,3-diol (AMMPDiol) in CDCl$_3$.
Figure 17:
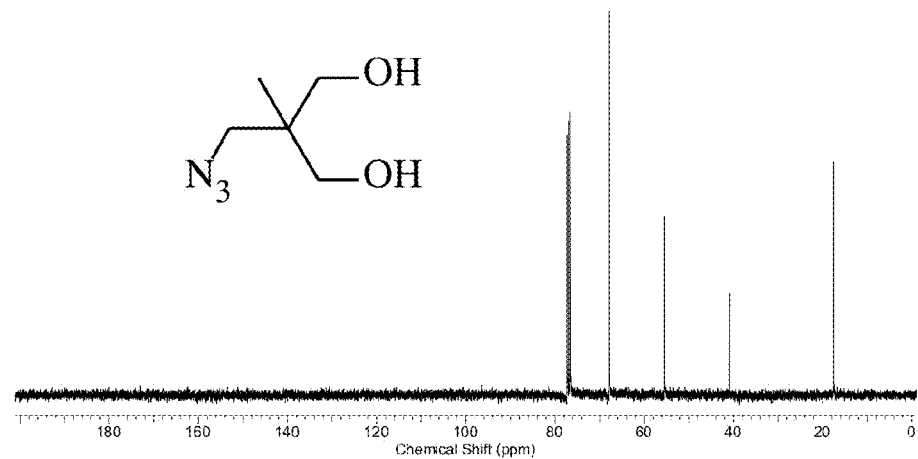
FIG. 17 shows representative $^{13}$C NMR of 2-(azidomethyl)-2-methylpropane-1,3-diol (AMMPDiol) in CDCl$_3$.

Into a 250-mL 3-neck flask equipped with a condenser, a thermometric and argon inlet, BMMPdiol (29.5 g, 0.16 mol) and sodium azide (26.0 g, 0.40 mmol) was dissolved in 120 mL of dimethyl sulfone. After reacting at 100° C. for 5 h, the solution was cooled down to room temperature and 100 mL of water and 20 g of sodium chloride were added. The solution was extracted with 200 mL ethyl ether for 4 times. The ether extract was combined and washed with 100 mL of saturated sodium chloride solution twice. After dying over anhydrous sodium sulfate, the solution was filtered through a 2-cm silica gel pad (60-230 mesh). The volatile was removed under vacuum, resulting in colorless oil, which turned into white crystal over time (16.8 g, yield=72.3%). $^1$H NMR (FIG. 16) (Chloroform-d, 400 MHz): δ(ppm) 3.59 (d, J=4.7 Hz, 4H), 3.44 (s, 2H), 2.60-2.60 (t, J=4.7 Hz, 2H), 0.85 (s, 3H). $^{13}$C NMR (FIG. 17) (Chloroform-d, 100 MHz): δ (ppm) 68.0, 55.5, 40.9, 17.5.

Synthesis of 5-(azidomethyl)-5-methyl-1,3-dioxan-2-one

Figure 18:
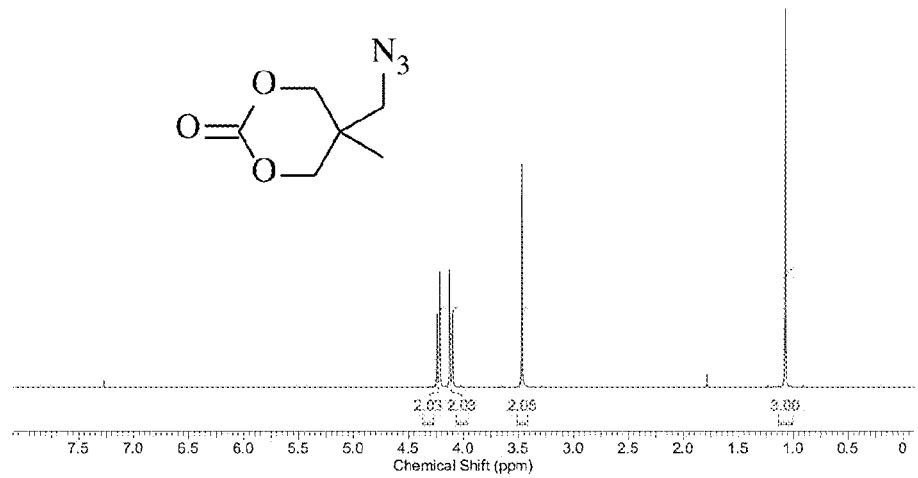
FIG. 18 shows representative $^1$H NMR of 5-(azidomethyl)-5-methyl-1,3-dioxan-2-one (AMMDXO) in CDCl$_3$.
Figure 19:
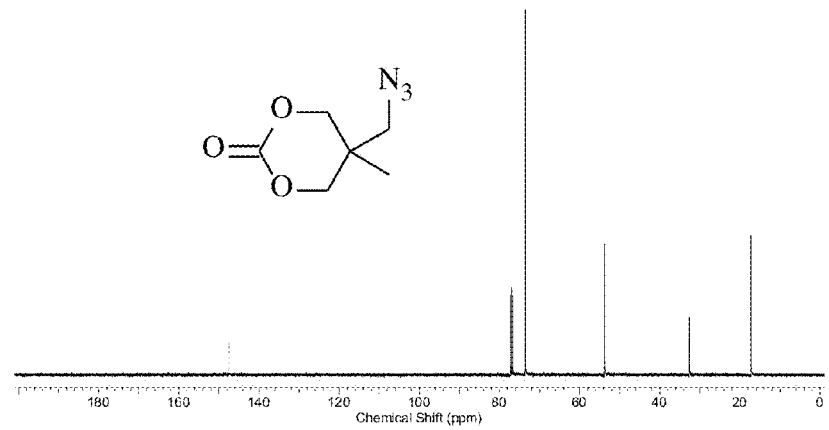
FIG. 19 shows representative $^{13}$C NMR of 5-(azidomethyl)-5-methyl-1,3-dioxan-2-one (AMMDXO) in CDCl$_3$.

Into a 500-mL 3-neck flask equipped with a condenser, a thermometer and argon inlet, ethyl chloroformate (28.48 g, 0.262 mol) was added into 350 mL of anhydrous tetrahydrofuran (THF) at −10° C. AMMPDiol (14.5 g, 0.10 mol) was dropped in 10 min and then 43.0 mL of triethylamine was dropped slowly in 1 h. After reacting for 5 h in the salt/ice bath and 20 h at room temperature, the solution was filtered and the filtrate was concentrated under vacuum. The resulting crude product was further purified by recrystallization in ethyl ether, which was repeated twice. A white crystal was obtained (14.1 g, yield=82.4%). $^1$H NMR (FIG. 18) (Chloroform-d, 400 MHz): δ(ppm) 4.18-4.28 (d, 2H), 4.05-4.16 (d, 2H), 3.47 (s, 2H), 1.07 (s, 3H). $^{13}$C NMR (FIG. 19) (Chloroform-d, 100 MHz): δ (ppm) 147.6, 73.5, 53.8, 32.6, 17.2.

Synthesis of Hydrophilic Cyclic Carbonate Monomer with Poly(Ethylene Glycol) Side Chain.

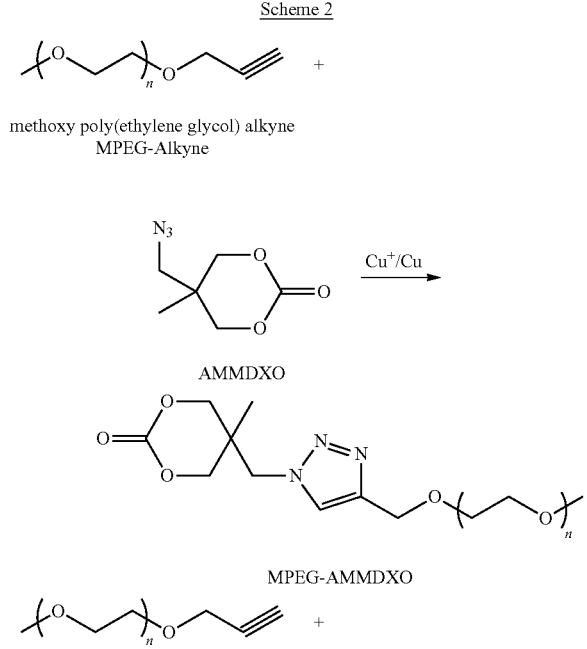

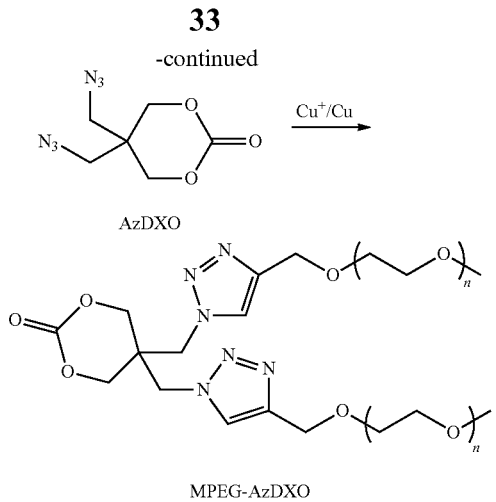

AzDXO

MPEG-AzDXO

Figure 20:
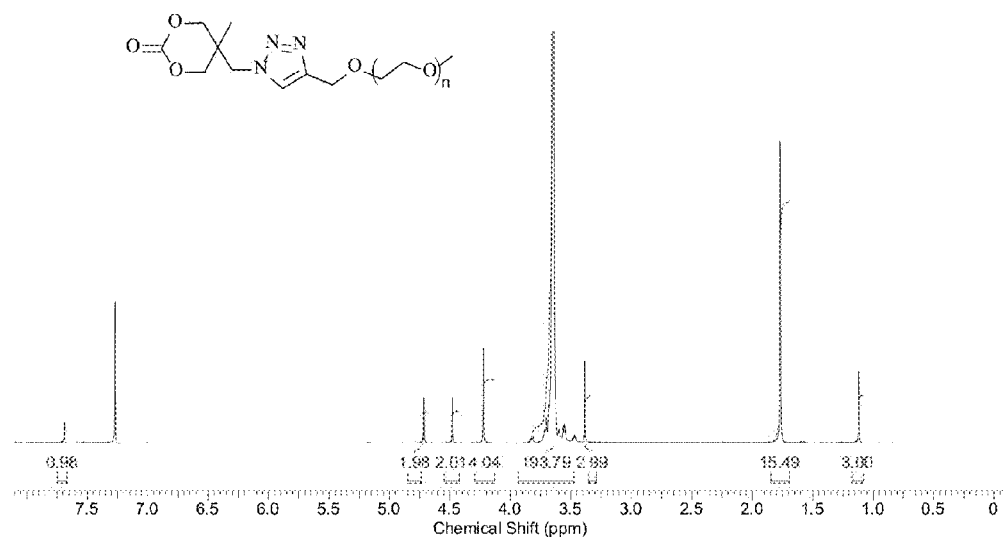
FIG. 20 shows representative $^1$H NMR of MPEG2k-AM-MDXO in CDCl$_3$.
Figure 21:
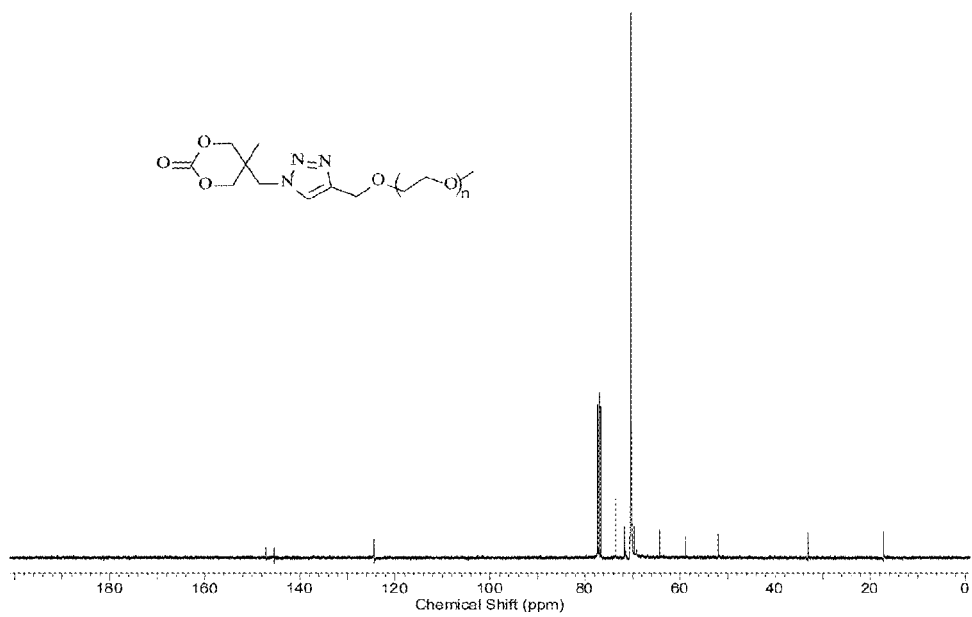
FIG. 21 shows representative $^{13}$C NMR of MPEG2k-AM-MDXO in CDCl$_3$.

A typical example of the synthesis of cyclic carbonate monomer with a single poly(ethylene glycol) side chain (Mn=2000): Into a 100-mL 2-neck flask, methoxy poly(ethylene glycol) alkyne (Mn~2000, 1.71 g, 0.857 mmol) and AMMDXO (0.164 g, 0.958 mmol) were dissolved in 50 mL of chloroform, and the solution was degassed and flushed with argon for 30 min before copper wire (55 mg, 0.865 mmol) and copper bromide (18.4 mg, 0.129 mmol) were added. After refluxing at 65° C. for 20 h, the solution was filtered and the filtrate was washed by 40 mL of 0.3M EDTA solution 6 times. The solution was dried over anhydrous sodium sulfate and then stirred with 4 g carbon black for 20 h. After filtering, the solution was concentrated to a final volume of ~10 mL and dropped into 100 mL of ethyl ether, and the formed precipitate was collected by filtration. After drying under vacuum, 1.70 g white powder was obtained (yield=89.8%). $^1$H NMR (FIG. 20) (Chloroform-d, 400 MHz): δ(ppm) 7.69 (s, 1H), 4.72 (s, 2H), 4.48 (s, 2H), 4.13-4.29 (m, 4H), 3.42-3.88 (m, 194H), 3.39 (s, 3H), 1.77 (s, 15H), 1.12 (s, 3H). $^{13}$C NMR (FIG. 21) (Chloroform-d, 100 MHz): δ (ppm) 147.2, 145.4, 124.4, 73.6, 71.7, 70.3, 69.7, 69.0, 64.4, 58.8, 51.9, 33.1, 17.2.

Cytocompatible Poly(Ethylene Glycol)-Co-Polycarbonate Hydrogels

Figure 22:
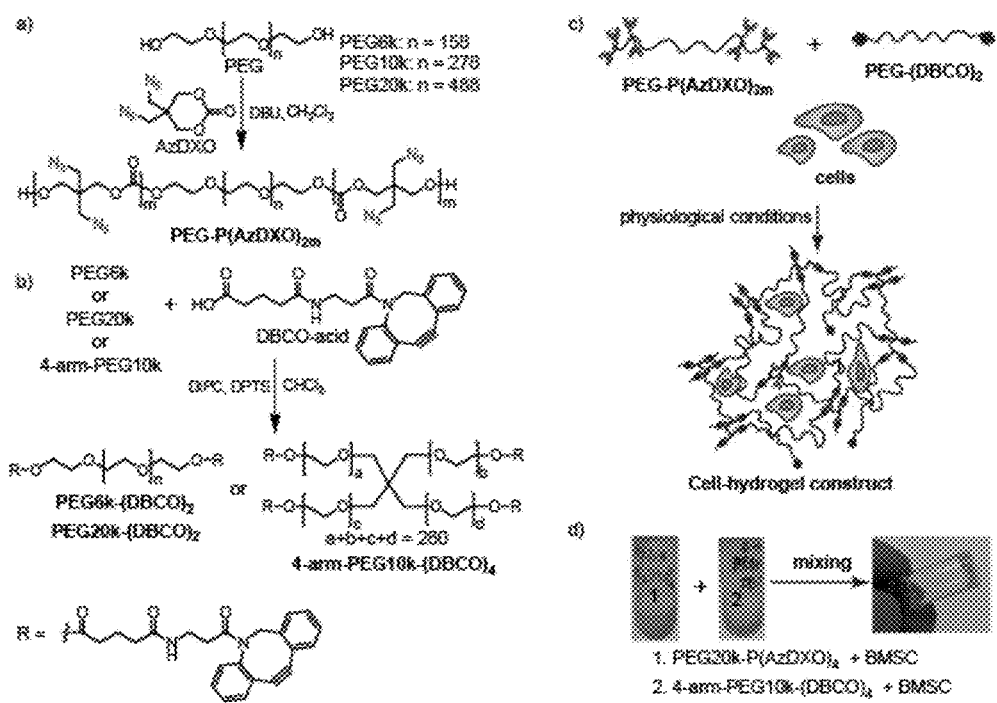
FIG. 22 shows macromer synthesis, crosslinking and cell encapsulation strategies: a) Ring-opening polymerization (ROP) of AzDXO initiated by PEG. [AzDXO]=0.1125 M, [DBU]=0.1 M, rt, Ar, 4 h; b) Synthesis of PEG-(DBCO)$_x$ by reacting DBCO-acid with PEG in CH$_2$Cl$_2$ under the catalysis of DIPC and DPTS, rt, 10 h; c) Depiction of the cell encapsulation by crosslinking PEG-P(AzDXO)$_{2m}$ and PEG-(DBCO)$_x$ via SPAAC "click" reaction; d) A representative demonstration of the rapid gellation of the cell-hydrogel constructs within 1 min of mixing the BMSC cell suspension (10$^6$ cells/mL) in a PEG20k-P(AzDXO)$_4$ solution (10 w/v % in expansion media) and a 4-arm-PEG10k-DBCO solution (10 w/v % in expansion). The BMSC expansion media consisted of α-MEM without ascorbic acid and 20% FBS.

As disclosed herein, the invention additionally provides a facile method for preparing PEG macromers flanked with aliphatic azido-functionalized biodegradable polycarbonate blocks (FIG. 22a), which are subsequently crosslinked with dibenzylcoclocyne (DBCO)-terminated PEG macromers (FIG. 22b) using copper-free, strain-promoted [3+2] azide-alkyne cylcloaddition (SPAAC) (FIG. 22c).

Figure 23:
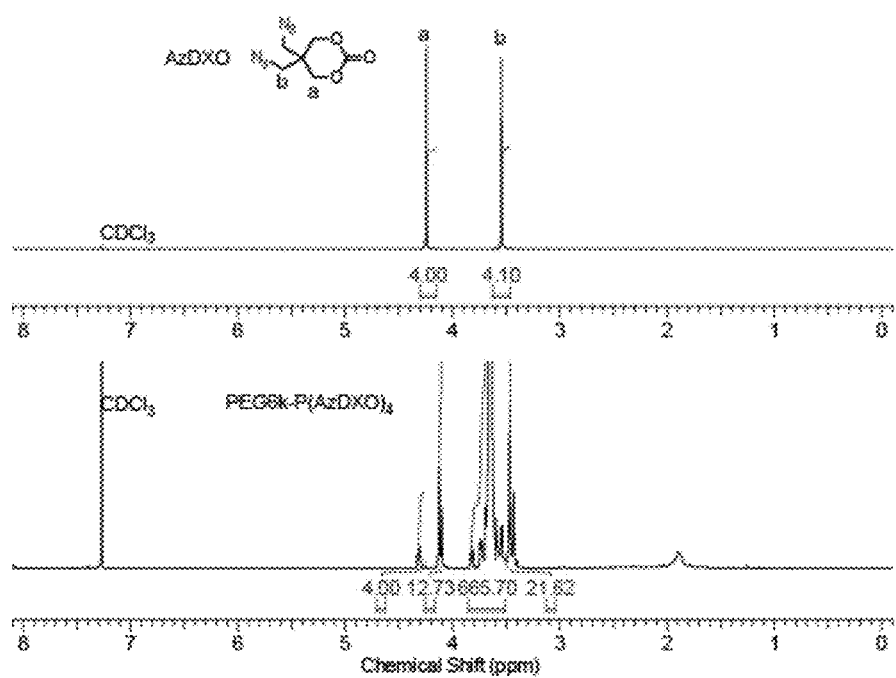
FIG. 23 shows representative $^1$H NMR spectra and proton integrations of PEG6k-P(AzDXO)$_4$ (bottom) supporting successful polymerization of AzDXO (top) initiated from the end hydroxyl groups of PEG6k. Proton integrations support a copolymer composition approximating that of the theoretical estimate.

The AzDXO monomer was synthesized in 2-steps as previously described. (Xu, et al. *Macromolecules*, 44, 2660.) Living/controlled ROP of AzDXO (0.1125 M) was initiated by varying amount of PEG6k, PEG10k and PEG20k using organocatalyst DBU in dichloromethane (0.01 M) at rt (FIG. 22a). The conversion of monomer reached ~90% in 4 h. Upon termination by benzoic acid, the PEG-P(AzDXO)$_{2m}$ macromer products were purified by repeated precipitation from dichloromethane in ethyl ether with >95% overall yield. As shown in Table 4, the P(AzDXO) block lengths (or degree of polymerization, DP) in the resulting tri-block macromers PEG-P(AzDXO)$_{2m}$ as determined by $^1$H NMR (FIG. 23) were close to the theoretical values (2m) calculated assuming 100% monomer conversion. GPC results revealed very narrow polydispersity of all PEG-P(AzDXO)$_{2m}$ (PDI: 1.02-1.09) with various PEG and P(AzDXO) block length combinations. The water solubility of macromer PEG-P(AzDXO)$_{2m}$ was dependent on the overall length of the P(AzDXO) blocks (Table 4). When the overall P(AzDXO) block length was shorter than 8 repeating units, the resulting PEG-P(AzDXO)$_{2m}$ was soluble in water regardless of the length of the PEG block.

By contrast, the triblock macromers became insoluble in water when the degree of polymerization of AzDXO was above the critical number of 8 regardless of the length of the initiating PEG (MW 6,000, 10,000 or 20,000). Similar phenomenon was observed in other amphiphilic triblock copolymers initiated by PEG. For example, Christine found that the triblock PEG-(PLA)$_2$ copolymers were insoluble in water when the lactic acid repeating units were greater than 22, regardless of the PEG block length investigated. (Hiemstra, et al. *Macromol. Symp.* 2005, 224, 119.)

TABLE 4

Characterizations of PEG-P(AzDXO)$_{2m}$ macromers

| Name[a] | DP[b] | $M_n^{NMR}$[c] | $M_n/N_3$[d] | $M_n^{GPC}$[e] | PDI[e] | Water solubility |
|---|---|---|---|---|---|---|
| PEG6k-P(AzDXO)$_4$ | 4.2 | 7909 | 946 | 12357 | 1.02 | soluble |
| PEG6k-P(AzDXO)$_7$ | 6.8 | 8465 | 622 | 12641 | 1.03 | soluble |
| PEG6k-P(AzDXO)$_8$ | 8.4 | 8805 | 523 | 12931 | 1.03 | cloudy |
| PEG6k-P(AzDXO)$_{11}$ | 10.8 | 9313 | 431 | 13168 | 1.03 | insoluble |
| PEG10k-P(AzDXO)$_{11}$ | 11.1 | 14658 | 662 | 20956 | 1.03 | insoluble |
| PEG20k-P(AzDXO)$_4$ | 3.6 | 22338 | 3079 | 36563 | 1.08 | soluble |
| PEG20k-P(AzDXO)$_9$ | 9.4 | 23573 | 1248 | 33380 | 1.09 | swellable |

[a]The naming of the samples reflects the approximate copolymer compositions including the averaged molecular weight of the initiating PEG and the degree of polymerization of the polycarbonate blocks;
[b]degree of polymerization of AzDXO determined from $^1$H NMR;
[c]number-averaged molecular weight calculated from $^1$H NMR;
[d]number-averaged molecular weight per azido group;
[e]number-averaged molecular weight and polydispersity index determined by GPC using an evaporative light scattering (ELS) detector.

Figure 24:
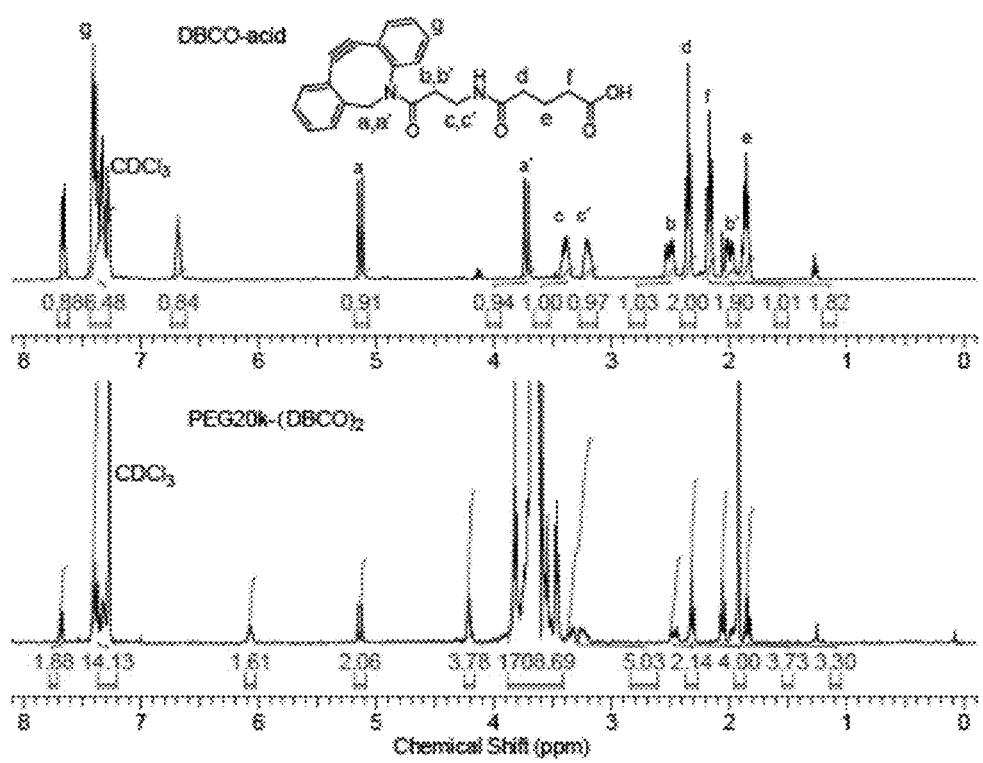
FIG. 24 shows representative $^1$H NMR spectra and proton integrations of PEG20k-(DBCO)$_2$ (bottom) supporting the successful attachment of DBCO-acid (top) on both ends of PEG20k.
Figure 27:
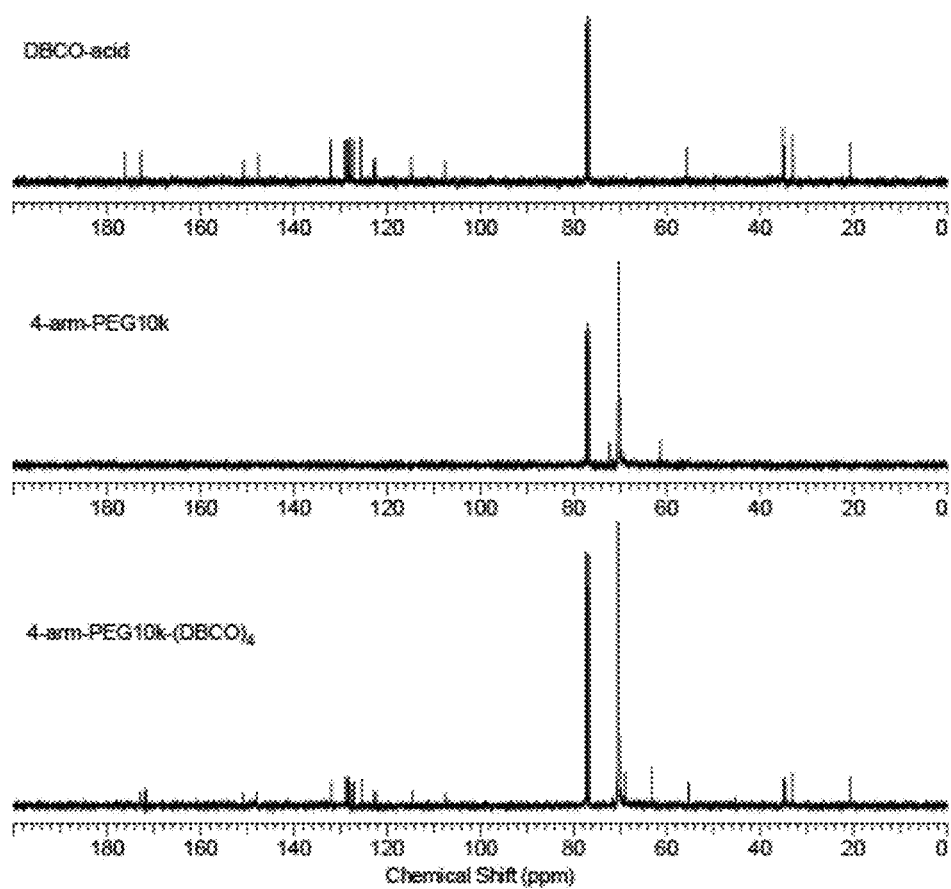
FIG. 27 shows representative $^{13}$C NMR of 4-arm-PEG10k-(DBCO)$_4$ showing the disappearance of the characteristic peak for —CH$_2$OH endgroups of 4-arm-PEG10k from 61.4 ppm, supporting complete esterification of —CH$_2$OH by DBCO-acid.

The linear or 4-arm DBCO-terminated PEG macromers, PEG-(DBCO)$_x$ (x=2 or 4), were synthesized by end-capping PEGs of various molecular weights and architectures (PEG6k, PEG20k or 4-arm-PEG10k) with DBCO-acid via esterification. The reaction were carried out in anhydrous dichloromethane with catalysts N,N'-diisopropylcarbodiimide (DIPC) and 4-(dimethylamino)-pyridinium p-toluenesulfonate (DPTS). The reactant ratio was kept as 1:1.5:5:0.25/hydroxyl end-groups in PEG:DBCO-acid:DIPC:DPTS. Complete esterification of the PEG end-groups was supported by the disappearance of the characteristic $^{13}$C NMR signal for —CH$_2$—OH from 61.4 ppm in the $^{13}$C NMR spectra of PEG-(DBCO)$_x$ (FIG. 27). The catalysts and by-products were readily removed by washing with water and subsequently precipitating in diethyl ether, or via sequential dialysis precipitation against diethyl ether and water. An overall high yields of >90% were obtained. As representatively shown in FIG. 24, the $^1$H NMR peak at 2.17 ppm corresponding to the methylene protons of —CH$_2$COOH of DBCO-acid was shifted to 2.05 ppm upon esterification with PEG20k, and a new peak at 4.22 ppm corresponding to the methylene protons of —CH$_2$OCO— in the resulting PEG20k-(DBCO)$_2$ appeared. The peak at 6.07 ppm in PEG20k-(DBCO)$_2$ and the peak at 6.67 ppm in DBCO-acid corresponded to the respective amide protons, the chemical shifts and intensities of which varied significantly with their concentrations and the water content in the NMR solvent. The $^{13}$C NMR (FIG. 27)

along with the $^1$H NMR integrations (FIG. 24) supported the successful attachment of DBCO-acid to all hydroxyl termini of the PEG.

Water soluble PEG-P(AzDXO)$_{2m}$ and PEG-(DBCO)$_x$ were dissolved in cell culture media, and in the presence of cell suspension, were readily mixed to form elastic cell-hydrogel construct under physiological conditions (FIG. 22d). Six different hydrogels were prepared using two PEG-P(AzDXO)$_{2m}$ macromers and three PEG-(DBCO)$_x$ macromers with different structures, compositions, and molecular weights for this study.

Figure 25:
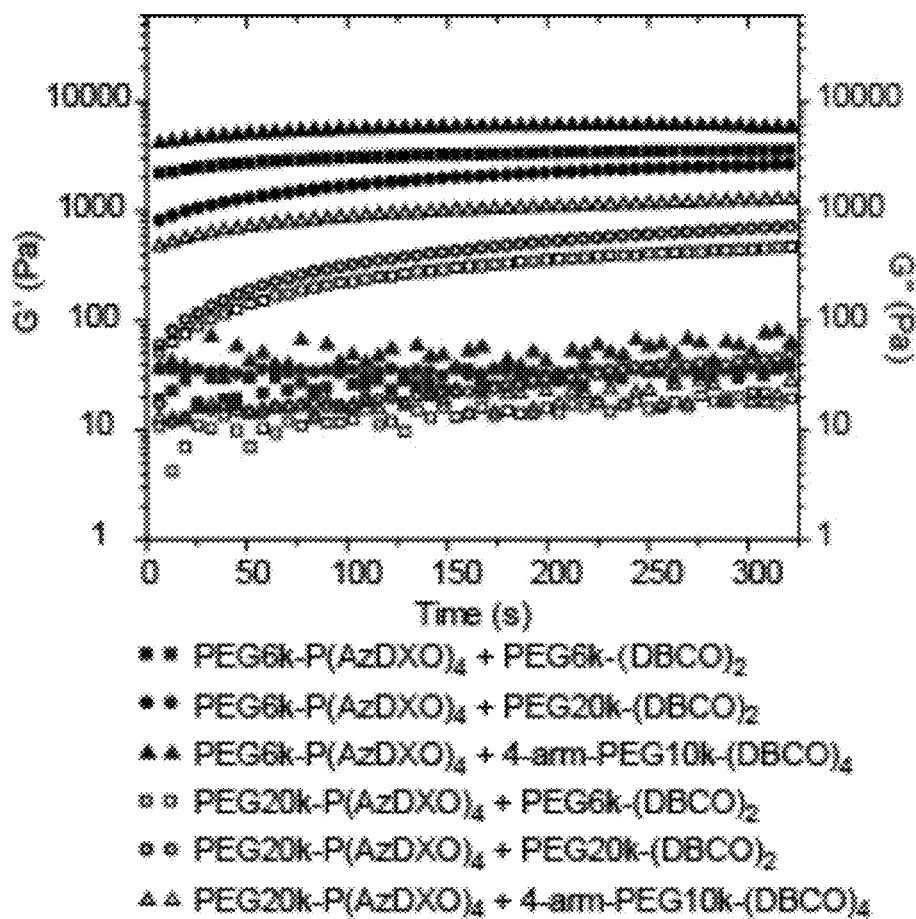
FIG. 25 shows time-dependent shear storage moduli (G', black symbols) and shear loss moduli (G", blue symbols) of the various hydrogel formulations during the SPAAC crosslinking.

To study the SPAAC crosslinking process between the PEG-P(AzDXO)$_2$m macromers and the PEG-(DBCO)$_x$ macromers and to determine the shear moduli of the crosslinked gels, time-sweep oscillatory rheology tests were carried out on the 6 formulations of the respective macromers (FIG. 25). Briefly, PEG-(DBCO)2 or 4-arm-PEG-(DBCO)4 solution (10 w/v %) was first loaded on the bottom plate of 20-mm parallel plates equipped with a Peltier heating unit (AR-2000 Rheometer, TA Instruments), before the aqueous solution of PEG-P(AzDXO)2m (10 w/v %) was added and rapidly mixed on plate by a pipette. The mixtures were equilibrated at 37° C. between the plates for 1 min prior to the test to ensure consistency among various formulations. As shown in FIG. 25, both the storage moduli (G') and loss moduli (G") of the mixtures increased with time and the recorded values levelled off after 300 sec, suggesting that the SPAAC crosslinking was completed within a matter of minutes. The sol-gel transition point, defined as the point where G' increased to across with G", was not observed using this testing protocol, likely due to the rapid occurrence of SPAAC crosslinking within the first minute of mixing the respective macromers. Indeed, rigorous quantitative comparisons of the gelling rates among the various fast-gelling formulations would be challenging without significant modification of the mixing and testing protocols. Qualitative observation of the gelling process by tilting the vials upon mixing the respective macromers revealed that the gelling rate followed the following trend: 4-arm-PEG10k-(DBCO)$_4$>PEG6k-(DBCO)$_2$>PEG20k-(DBCO)$_2$ upon mixing with PEG-P(AzDXO)$_{2m}$. All formulations started to gel in less than 1 min by the vial tilting test (FIG. 22d), consistent with the implications derived from the time-sweep oscillatory rheology tests (FIG. 25). Such a fast gelling rate will be beneficial for applications of the macromers as injectable hydrogel formulations to repair tissue defects where the containment of the hydrogel within the local environment is critical.

The equilibrium shear modulus of the hydrogel can be tuned by adjusting the length between the reactive groups (PEG block length) or macromer structures (linear vs. 4-arm). As shown in FIG. 25, at the same weight content (10 w/v %), hydrogels crosslinked from PEG-(DBCO)$_x$ and PEG6k-P(AzDXO)$_4$ (solid symbols) exhibited higher storage moduli than those crosslinked from PEG-(DBCO)$_x$ and PEG20k-P(AzDXO)$_4$ (open symbols), suggesting that the storage modulus inversely correlated with the PEG length between the P(AzDXO) blocks. Among all 6 formulations, the hydrogel crosslinked by PEG6k-P(AzDXO)$_4$ and 4-arm-PEG10k-(DBCO)$_4$ exhibited the highest storage modulus throughout the gelling process, with its equilibrium G' approaching 6.0 KPa. This is largely due to the highest chemical crosslinking density accomplished by the 4-armed DBCO crosslinker and the PEG-P(AzDXO)$_{2m}$ with the shortest PEG block length. In addition to chemical crosslinking density, degree of physical entanglement also played an important role in the storage modulus of the gel, especially when both macromers contain sufficiently long PEG blocks. For instance, the gel crosslinked by PEG20k-P(AzDXO)$_4$ and PEG20k-(DBCO)$_2$ exhibited higher modulus than that crosslinked by PEG20k-P(AzDXO)$_4$ and PEG6k-(DBCO)$_2$. Overall, the equilibrium shear moduli of the 6 gel systems decrease in the following order: PEG6k-P(AzDXO)$_4$+4-arm-PEG10k-(DBCO)$_4$ (6 KPa)>PEG6k-P(AzDXO)$_4$+PEG6k-(DBCO)$_2$ (3.5 kPa) >PEG6k-P(AzDXO)$_4$+PEG20k-(DBCO)$_2$ (2.7 kPa) >PEG20k-P(AzDXO)$_4$+4-arm-PEG10k-(DBCO)$_4$ (1.3 kPa) >PEG20k-P(AzDXO)$_4$+PEG20k-(DBCO)$_4$ (0.7 kPa) >PEG20k-P(AzDXO)$_4$+PEG6k-(DBCO)$_2$ (0.5 kPa).

Figure 26:
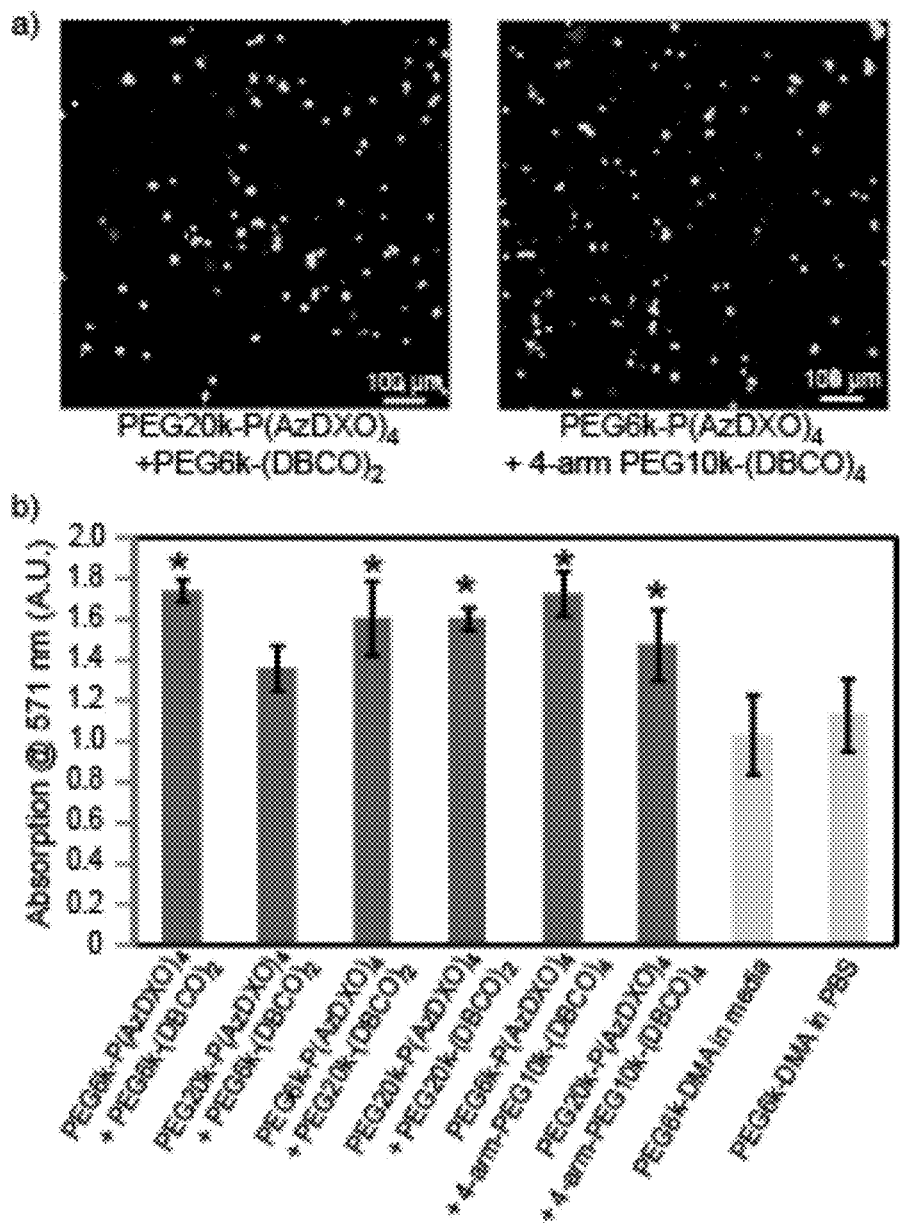
FIG. 26 shows viability of BMSC cells encapsulated by the "click" hydrgles. (a) Representative confocal Z-stack (400 μm) images of encapsulated BMSC cells stained with a live/dead viability staining kit 24 h after initial encapsulation. Live cells were stained green while dead cells were stained red; (b) MTT cell viability assay performed on the hydrogel-BMSC constructs ($10^6$ cells/mL) 48 h after cell encapsulation showing better cell viability for all "click" hydrogel-encapsulated BMSCs than those photocrosslinked PEG6k-DMA hydrogels. * indicates p<0.05 (student t-test) between the "click" gel and the PEG6k-DMA control (crosslinked in the media).
Figure 28:
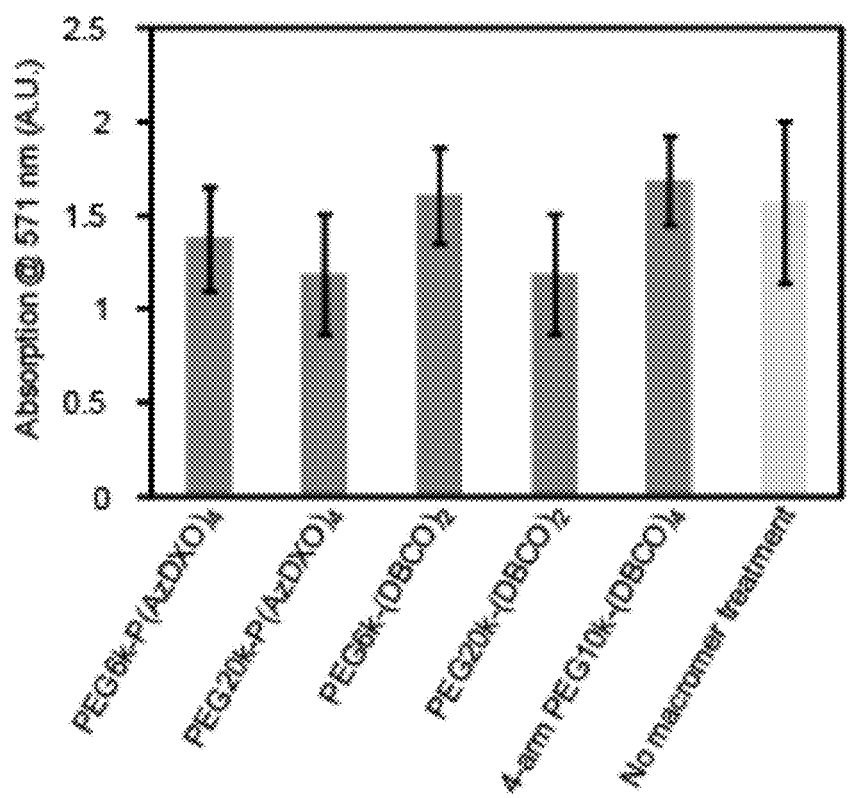
FIG. 28 shows MTT viability assay of BMSC cells cultured on 96-well tissue culture plates in the presence of PEG-P(AzDXO)$_{2m}$ and PEG-(DBCO)$_x$ macromers showing cell viability at 48 h comparable to those cultured in the absence of any macromers. For cell seeding, BMSC cell suspension ($10^6$ cells/mL, 50 μL) in expansion media (α-MEM without ascorbic acid, 20% FBS) containing 0 or 10 w/v % macromers was added to each well of the 96-well plate before an extra 200 μL of expansion media was added. No statistically significant difference was observed between any of the macromer-treated cultures and the no-macromer control culture (p>0.05; student t-test).

The cytocompatibility of PEG-P(AzDXO)$_{2m}$ and PEG-(DBCO)$_x$ macromers and the respective "click" hydrogels were evaluated in vitro. Bone marrow-derived stromal cells (BMSC) cultured in the presence of 10 w/v % of each macromer showed comparable cell viability at 48 h to those cultured without any macromer supplements (FIG. 28), supporting excellent cytocompatibility of these macromers. Further, we showed that most BMSCs encapsulated by "clicking" the macromer components (FIG. 22d) remained viable, as supported by the dominant green fluorescent stains for live cells observed at 24 h upon performing a live/dead cell staining on the cell-hydrogel constructs (FIG. 26a). No statistically significant difference in the hydrogel storage modulus was detected upon the encapsulation of BMSC in any of the formulations investigated.

MTT cell viability assay performed on the hydrogel-cell constructs 48 h after cell encapsulation (FIG. 26b) showed that BMSC cells encapsulated in all "click" hydrogels (10$^6$ cells/mL) exhibited higher viability than those photo-encapsulated in the PEG6k-DMA hydrogel that was widely used for cell encapsulation in cartilage engineering. (Bryant, et al. *J. Biomed. Mater. Res.* 2002, 59, 63; Elisseeff, et al. *J. Biomed. Mater. Res.* 2000, 51, 164.) In our hands, the gellation of the 10 w/v % PEG6k-DMA gels in the presence of BMSC (10$^6$ cells/mL) and 0.05 w/v % Irgacure-2959 photoinitiator required irradiation at 365 nm for 10 min. It is known that environmental conditions such as oxygen level could lead to variation in the required polymerization time. The consistently more rapid gelling (within 1 min for most formulations) enabled by the SPAAC crosslinking presented here, coupled with the eliminated need for toxic photoinitiators or UV irradiation, presents a significant advantage.

Experimental Section

Chemicals.

Azido-functionalized cyclic carbonate monomer (AzDXO) was synthesized as described previously. (Xu, et al. *Macromolecules*, 44, 2660.) Poly(ethylene glycol)diol (PEG, M$_n$=6,000, 10,000, 20,000 g/mol, Aldrich) and 4-arm-PEG (Mn=10,000 g/mol, JenKem Technolgoy) were dried under vacuum in melt state for 3 h prior to use. 1,8-Diazabicyclo [5.4.0]undec-7-ene (DBU) was purified by distillation with calcium hydride under reduced pressure. Dichloromethane and chloroform were dried by distillation over P$_2$O$_5$ immediately prior to use. All other chemicals were used as received.

Synthesis of PEG-P(AzDXO)$_{2m}$

PEG-P(AzDXO)$_{2n}$ macromers were prepared by initiating ROP of AzDXO with PEG6k, PEG10k or PEG20k under the catalysis of DBU at rt in CH$_2$Cl$_2$. The AzDXO concentration and DBU concentration were kept at 0.1125 M and 0.01 M, respectively. The amount of PEG was adjusted accordingly to obtained various copolymer compositions shown in Table 1. In a representative procedure for synthesizing PEG6k-P(AzDXO)$_4$, PEG6k (6.00 g, 1.00 mmol) and AzDXO (0.955 g, 4.50 mmol) were dissolved in 38 mL of CH$_2$Cl$_2$ under argon atmosphere. A 2-mL solution of DBU (0.2 M in CH$_2$Cl$_2$) was injected to initiate the polymerization.

After 4 h, benzoic acid (0.122 g, 1.0 mmol) was added to neutralize DBU. The polymer was purified by precipitation in 800 mL of ethyl ether. The precipitate was then redissolved in 40 mL of $CH_2Cl_2$ and precipitated again in 800 mL of ethyl ether, and repeated twice. The macromer was obtained as white powder and dried under vacuum at rt (6.740 g, yield=97%).

Synthesis of PEG-(DBCO)$_x$.

The alkyne-containing macromers PEG-(DBCO)$_x$ were synthesized by esterification of the hydroxyl ends of the respective linear PEG or 4-arm-PEG with DBCO-acid. In a representative synthesis of PEG-(DBCO)$_x$ with high $M_n$, PEG20k (4.0 g, ~0.2 mmol) was dissolved in 20 mL of chloroform. DBCO-acid (234.3 mg, 0.6 mmol), 4-(dimethylamino)-pyridinium p-toluenesulfonate (DPTS, 29.4 mg, 0.1 mmol) and N,N-diisopropylcarbodiimide (DIPC, 252.4 mg, 2.0 mmol) were added subsequently. After 10 h, 80 mL of chloroform was added and the solution was washed by 20 mL of 0.1 M NaCl aqueous solution three times. The organic layer was dried with anhydrous sodium sulfate overnight. After filtering, the clear solution was dropped into 900 mL of ethyl ether, and the white precipitate was collected by filtration. The solid was redissolved in 100 mL of chloroform and reprecipitated in 900 mL of ethyl ether and repeated twice until no residue catalysts could be detected by $^1H$ NMR. The macromer was obtained as white powder and dried under vacuum at rt (4.05 g, yield=97.4%).

NMR and GPC. $^1H$ (400 MHz) and $^{13}C$ NMR (100 MHz) spectra were recorded on a Varian INOVA-400 spectrometer in deuterated chloroform ($CDCl_3$, 99.8 atom % D with 0.03% v/v TMS). GPC measurements were taken on a Varian ProStar HPLC system equipped with two 5-mm PLGel Mini-MIX-D columns (Polymer Laboratory, Amherst, Mass.), a UV-vis detector and a PL-ELS2100 evaporative light scattering detector (Polymer Laboratory, Amherst, Mass.). THF was used as an eluent at a flow rate of 0.3 mL/min at rt. The number-averaged molecular weight ($M_n$) and the polydispersity index (PDI) were calculated by a Cirrus AIA GPC Software using narrowly dispersed polystyrenes (ReadyCal kits, PSS Polymer Standards Service Inc. Germany) as calibration standards.

Rheology.

Dynamic rheology test was performed on an AR-2000 rheometer (TA Instruments) equipped with 20-mm parallel plates and a Peltier heating unit. The gelling process of the various formulations and the evolution of the shear modulus of the hydrogels were studied by oscillatory time sweep rheology experiments at 37° C. Aqueous solutions of PEG-P(AzDXO)$_2$m and PEG-(DBCO)$_x$ (10 w/v %) in cell expansion media (α-MEM without ascorbic acid, 20% FBS) with 1:1 molar ratio of the azide groups to the alkyne groups were loaded on the bottom plate sequentially and mixed by pipette. The mixed solution was kept between the parallel plates for 60 sec before the experiment and data collection were initiated to ensure consistency among various formulations. An oscillatory frequency of 1 Hz and a strain of 0.5% were applied.

Bone Marrow Stromal Cell (BMSC) Encapsulations.

PEG-P(AzDXO)$_{2m}$ and PEG-(DBCO)$_x$ were dissolved in BMSC expansion media to reach a 10 w/v % concentration, respectively. The solutions were sterile-filtered through a 0.22-μm filter. BMSC were harvested from the femur and tibia of skeletally mature male rats (Charles River SASCO SD) and enriched by adherent culture as previously described. (Song, et al. *J. Biomed. Mater. Res.*, Part A 2009, 89A, 1098.) Passage 1 BMSC cells were plated overnight in expansion media, trypsinized, counted and suspended into the respective macromer solutions ($10^6$ cells/mL). The two BMSC-macromer solutions, PEG-P(AzDXO)$_{2m}$ and PEG-(DBCO)$_x$, were mixed in a total volume of 50 μL in 96-well tissue culture plate. An extra 200 μL of expansion media was added to each well after 45 min. As a control hydrogel for BMSC encapsulation, poly(ethylene glycol)dimethylacrylate (PEGDMA Mn~6000 g/mol) was also photo-crosslinked in the presence of BMSC cells. PEGDMA (10 w/v %) and the photo initiator Irgacure-2959 (0.05 w/v %) were dissolved in PBS (pH 7.4) or BMSC expansion media. The passage 1 BMSC cells were suspended in 50 μL of PEGDMA/Irgacure-2959 solution ($10^6$ cells/mL) and irradiated with 365 nm UV light for 10 min. An extra 200 μL of expansion media was added to each well immediately after the photo-polymerization. All cell-hydrogel constructs were cultured for 24 and 48 h in a humidified incubation (5% $CO_2$, 37° C.) before being subjected to live/dead cell staining or MTT cell viability assay. A sample size of 3 was applied to all cell-hydrogel constructs cultured for MTT.

Live and Dead Cell Staining of the Hydrogel-BMSC Constructs.

The hydrogel-cell constructs were stained using a LIVE/DEAD® viability/cytotoxicity kit (Molecular Probes) according the vendor's protocol. Living cells will be stained with green fluorescence by intracellular esterase catalyzed hydrolysis of Calcein AM, and dead cells will be stained red by Ethidium homodimer-1 after penetrating through the damaged membranes and binding of with nucleic acids. The stained hydrogel-cell construct was mounted on microscope slide and imaged by a Leica SP laser scanning confocal microscope. Confocal Z-stack images of encapsulated BMSC cells over the depth of 400 μm (20 consecutive 20-μm slices) were overlaid.

MTT Cell Viability Assay.

The viability of the MBSC cells cultured on tissue culture plate in the presence of 10 w/v % macromers or those encapsulated in 3-D hydrogels were evaluated using MTT cell proliferation kit (Roche) after 48-h culture in expansion media (α-MEM without ascorbic acid, 20% FBS) in 96-well plates. To a total volume of 150 μl of culture media and cell-hydrogel construct, 15 μl of MTT labelling reagent was added and incubated for 8 h at 37° C. on an orbital shaker. A 150-μl solubilization solution was then added to each well, and incubated at 37° C. on the orbital shaker for 36 h to fully dissolve and release the purple formazan crystals from the 3-D hydrogels. The absorbance at 571 nm was read on a MULTISCANFC spectrophotometer (Thermo Scientific). A sample size of 3 was applied to each construct or culture condition.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

What is claimed is:
1. A compound having the structural formula of:
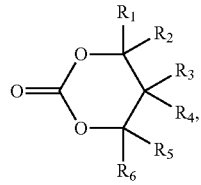
wherein each of $R_1$, $R_2$, $R_5$ and $R_6$ is H; and each of $R_3$ and $R_4$ is —$(CH_2)_p$—$N_3$, wherein p is an integer from about 1 to about 16.
2. The compound of claim 1, wherein p=1.
* * * * *